US010426335B2

(12) United States Patent
Akiba et al.

(10) Patent No.: US 10,426,335 B2
(45) Date of Patent: Oct. 1, 2019

(54) OPHTHALMIC IMAGE DISPLAY DEVICE AND OPHTHALMIC IMAGING DEVICE

(71) Applicant: KABUSHIKI KAISHA TOPCON, Itabashi-ku, Tokyo (JP)

(72) Inventors: Masahiro Akiba, Toda (JP); Atsushi Kubota, Tokyo (JP)

(73) Assignee: KABUSHIKI KAISHA TOPCON, Itabashi-ku, Tokyo (JP)

( * ) Notice: Subject to any disclaimer, the term of this patent is extended or adjusted under 35 U.S.C. 154(b) by 0 days.

(21) Appl. No.: 15/565,542

(22) PCT Filed: Jan. 21, 2016

(86) PCT No.: PCT/JP2016/051747
§ 371 (c)(1),
(2) Date: Oct. 10, 2017

(87) PCT Pub. No.: WO2016/167001
PCT Pub. Date: Oct. 20, 2016

(65) Prior Publication Data
US 2018/0116501 A1 May 3, 2018

(30) Foreign Application Priority Data

Apr. 14, 2015 (JP) ................. 2015-082876

(51) Int. Cl.
*A61B 3/14* (2006.01)
*A61B 3/10* (2006.01)
(Continued)

(52) U.S. Cl.
CPC ............ *A61B 3/102* (2013.01); *A61B 3/0025* (2013.01); *A61B 3/14* (2013.01); *A61B 5/0066* (2013.01);
(Continued)

(58) Field of Classification Search
CPC ........... A61B 3/103; A61B 3/14; A61B 3/113; A61B 3/1225; A61B 3/024; A61B 3/032; A61B 3/18; A61B 3/1015
(Continued)

(56) References Cited

U.S. PATENT DOCUMENTS

2007/0216909 A1* 9/2007 Everett ................ A61B 5/0059
356/479
2008/0151187 A1* 6/2008 Tsukada ................ A61B 3/102
351/206
(Continued)

FOREIGN PATENT DOCUMENTS

JP 2009-165710 A 7/2009
JP 2010-523286 A 7/2010
(Continued)

OTHER PUBLICATIONS

International Search Report dated Mar. 1, 2016, in connection with International Patent Application No. PCT/JP2016/051747, 2 pgs.

*Primary Examiner* — Dawayne Pinkney
(74) *Attorney, Agent, or Firm* — Chiesa Shahinian & Giantomasi PC

(57) ABSTRACT

An ophthalmic image display device having, a display controller that displays a B mode image, a blood vessel enhanced image representing a same cross section as the B mode image, and one or more front images individually formed based on a three dimensional data set acquired by performing optical coherence tomography on a subject's eye in a predetermined layout. Further, the display controller displays a cross section position indicator that indicates a position of a cross section of the B mode image over at least one of the one or more front images. In addition, the display controller synchronously performs changing of a display position of the cross section position indicator and updating of a display of each of the B mode image and the blood
(Continued)

vessel enhanced image in accordance with an operation for moving the cross section position indicator performed using an operation unit.

20 Claims, 9 Drawing Sheets

(51) Int. Cl.
  *A61B 3/02* (2006.01)
  *A61B 3/00* (2006.01)
  *G01N 21/17* (2006.01)
  *A61B 5/00* (2006.01)
(52) U.S. Cl.
  CPC ........... *A61B 5/0073* (2013.01); *G01N 21/17* (2013.01); *A61B 3/0058* (2013.01)
(58) Field of Classification Search
  USPC ....... 351/206, 200, 205, 209, 210, 221, 222, 351/245, 246, 239
  See application file for complete search history.

(56) References Cited

U.S. PATENT DOCUMENTS

| | | |
|---|---|---|
| 2009/0005691 A1 | 1/2009 | Huang et al. |
| 2010/0238403 A1* | 9/2010 | Kobayashi ........... A61B 3/0058 351/206 |
| 2012/0194783 A1 | 8/2012 | Wei et al. |
| 2015/0313466 A1 | 11/2015 | Yoshida |
| 2016/0135683 A1 | 5/2016 | Yasuno et al. |
| 2016/0302738 A1 | 10/2016 | Yoshida et al. |
| 2016/0310024 A1 | 10/2016 | Yoshida et al. |

FOREIGN PATENT DOCUMENTS

| | | |
|---|---|---|
| JP | 2013-116382 A | 6/2013 |
| JP | 2013-116424 A | 6/2013 |
| JP | 2013-184018 A | 9/2013 |
| JP | 2014-057899 A | 4/2014 |
| JP | 2015-000131 A | 1/2015 |

* cited by examiner

OPHTHALMIC IMAGE DISPLAY DEVICE AND OPHTHALMIC IMAGING DEVICE

CROSS-REFERENCE TO RELATED APPLICATIONS

This application is a national stage (under 35 U.S.C. 371) of International Patent Application No. PCT/JP2016/051747, filed Jan. 21, 2016, claiming priority to Japanese Patent Application No. 2015-082876, filed Apr. 14, 2015, both of which are herein incorporated by reference in their entirety.

FIELD

Embodiments described herein relate generally to an ophthalmic image display device and an ophthalmic imaging device.

BACKGROUND

Diagnostic imaging occupies an important position in the field of ophthalmology. In recent years, utilization of optical coherence tomography (OCT) has advanced. OCT is being used not only for acquiring B mode images and three dimensional images of a subject's eye but also for acquiring front images (also referred to as en-face images) such as C mode images and shadowgrams. In addition, OCT is also used for acquiring an image in which a specific site of the subject's eye is emphasized, and acquiring functional information. For example, it is possible to construct a B mode image or a front image in which retinal blood vessels and choroidal blood vessels are emphasized (referred to as a blood vessel enhanced image or an angiogram) based on time series volume data acquired using OCT. Furthermore, a rendering method and a graphical user interface (GUI) for observing a desired slice of the subject's eye have been proposed.

Patent Document 1: US Unexamined Patent Application Publication No. 2012/0194783;
Patent Document 2: Japanese Unexamined Patent Application Publication No. 2013-184018;
Patent Document 3: Japanese Unexamined Patent Application Publication (Translation of PCT Application) No. 2010-523286;
Patent Document 4: Japanese Unexamined Patent Application Publication No. 2009-165710;
Patent Document 5: Japanese Unexamined Patent Application Publication No. 2015-000131.

In the ophthalmic diagnostic imaging, a plurality of images is referred sequentially or as a list. Particularly in OCT diagnostic imaging, the user observes various types of images such as B mode images, front images, morphological images, functional images, and so on. while appropriately changing slice position and slice thickness. However, it has been difficult to smoothly and promptly perform such observation with conventional techniques. For example, when performing observation while switching display images as necessary, it is not possible to re-display the images displayed previously and the images displayed before the previous image with the conventional techniques. Therefore, it has been difficult to smoothly compare the images before and after switching. Further, according to the conventional technique, it is not possible to display in parallel a plurality of images to which similar parameter setting has been applied. Therefore, it is necessary to perform a troublesome work of displaying the next image while confirming the setting contents at the time of switching the display image.

SUMMARY

The object of the present invention is to facilitate and speed up ophthalmic diagnostic imaging.

An ophthalmic image display device according to an embodiment includes a display controller configured to display information on a display means, and an operation unit. The display controller displays a B mode image, a blood vessel enhanced image representing a same cross section as the B mode image, and one or more front images individually formed based on a three dimensional data set acquired by performing optical coherence tomography on a subject's eye in a predetermined layout. Further, the display controller displays a cross section position indicator that indicates a position of a cross section of the B mode image over at least one of the one or more front images. In addition, the display controller synchronously performs changing of a display position of the cross section position indicator and updating of a display of each of the B mode image and the blood vessel enhanced image in accordance with an operation for moving the cross section position indicator performed using the operation unit.

According to the embodiment, ophthalmic diagnostic imaging can be performed smoothly and promptly.

DETAILED DESCRIPTION

Figure 1:
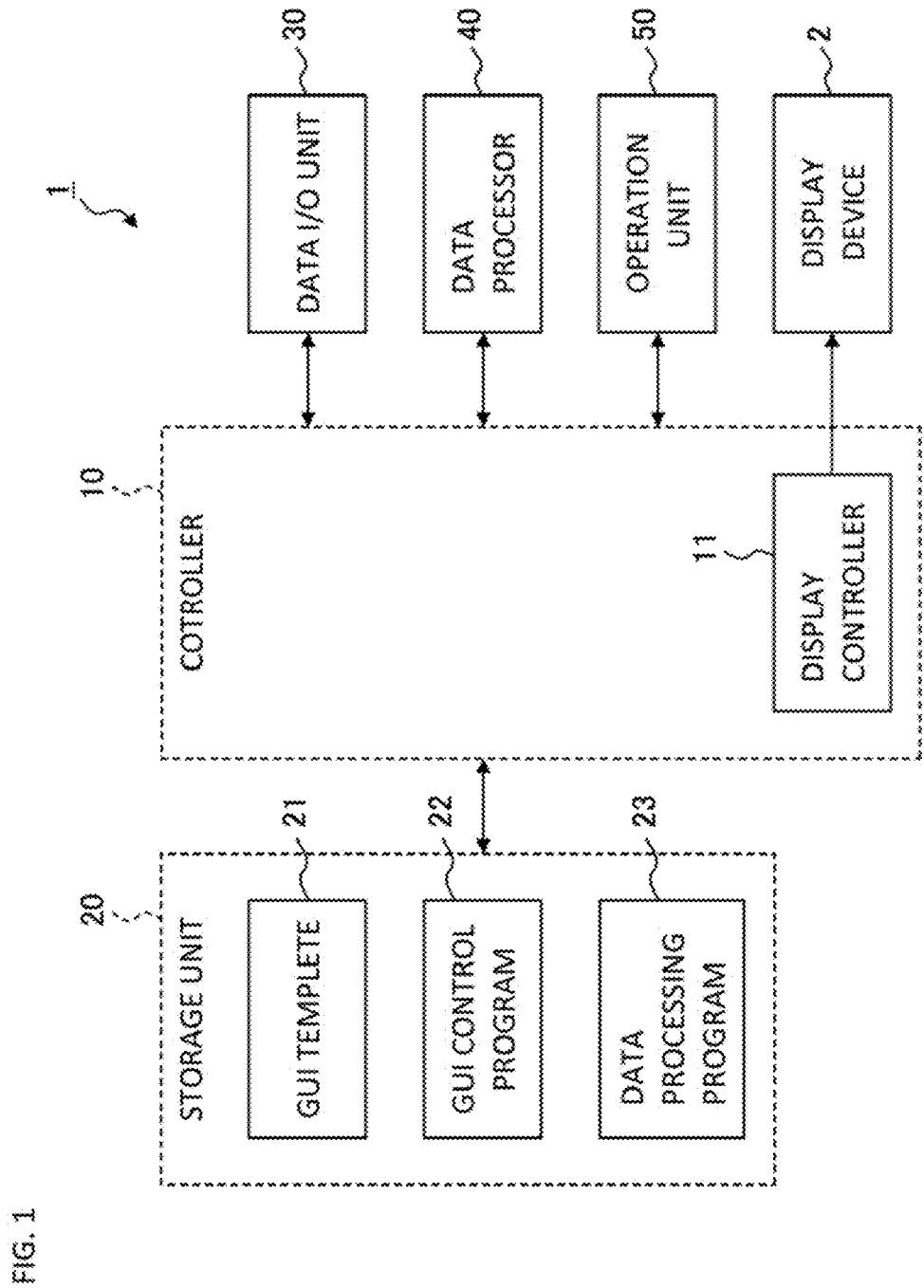
FIG. 1 is a schematic diagram illustrating an example of the configuration of an ophthalmic image display device according to an embodiment.

Exemplary embodiments of the present invention will be described with reference to the drawings. The contents of the documents cited in the present specification can be incorporated into the embodiments.

The embodiments provide a GUI for observing images of a subject's eye. The GUI is used to observe at least OCT images. The OCT images may include: an image of an arbitrary cross section mode (e.g., a B mode image, a C mode image, a multiplanar reconstruction (MPR) image, or the like); a shadowgram formed by projecting an arbitrary area of a three dimensional data set (e.g., volume data, stack data, or the like); and a blood vessel enhanced image (referred to as an angiogram) formed based on a three dimensional data set constructed from a plurality of two dimensional data sets acquired through iteratively scanning substantially the same area of the subject's eye. The three dimensional data set can be acquired, for example, by scanning each of a plurality of B cross sections B1, B2, . . . , Bn a predetermined number of times (for example, four times), forming a predetermined number of B mode images of each B cross section Bi (i=1, 2, . . . , n), and embedding the B mode images in the same three dimensional coordinate system (furthermore, by voxelizing the B mode images embedded in the same three dimensional coordinate system). Such an image forming technique is known.

The ophthalmic image display device of the embodiment may or may not have a function of forming an image from the three dimensional data set (i.e., rendering function). In the case of having the rendering function, the ophthalmic image display device may be configured to acquire a three dimensional data set acquired by an ophthalmic OCT apparatus via a network (e.g., in-house LAN, or the like) or via a recording medium and renders the three-dimensional data set according to an instruction from a user or a computer, thereby forming an image for observation. On the other hand, in case of not having the rendering function, the ophthalmic image display device may be configured to be capable of communicating with an external computer (e.g., a server, or the like) having the rendering function via a network in real time, transmits an instruction from a user or the like to the external computer, and receives an image for observation formed by the external computer according to the instruction. Note that the ophthalmic image display device may or may not include a display device on which an image is displayed.

The ophthalmic imaging device of the embodiment includes an ophthalmic image display device having the rendering function, and includes an optical system, a driving system, a control system, and a data processing system each for performing OCT. The ophthalmic imaging device is configured to be capable of performing, for example, Fourier domain OCT. The Fourier domain OCT includes spectral domain OCT and swept source OCT. The spectral domain OCT is a technique of imaging a subject's eye by acquiring the spectra of interference light in a space-divisional manner using a broadband low coherence light source and a spectrometer and by subjecting the spectra to Fourier transform. The swept source OCT is a technique of imaging a subject's eye by acquiring the spectra of interference light by time-divisional manner using a wavelength sweep light source (also referred to as a wavelength tunable light source) and a photodetector (e.g., a balanced photodiode or the like) and subjecting the spectra to Fourier transform. The ophthalmic imaging device may include a modality other than OCT. Such a modality may be a fundus camera, a scanning laser ophthalmoscope (SLO), a slit lamp microscope, an ophthalmic surgical microscope, or the like.

<Ophthalmic Image Display Device>
[Configuration]

An embodiment of an ophthalmic image display device will be described. FIG. 1 shows an exemplary configuration of the ophthalmic image display device. The ophthalmic image display device 1 controls the display device 2 to display a GUI for observing images of the subject's eye and various information relating to the subject's eye. The display device 2 may be a part of the ophthalmic image display device 1 or may be an external device connected to the ophthalmic image display device 1.

The ophthalmic image display device 1 includes the controller 10, the storage unit 20, the data input and output unit 30, the data processor 40, and the operation unit 50.

The controller 10 controls each part of the ophthalmic image display device 1. The controller 10 includes a processor. In the present specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), a field programmable gate array (FPGA)), or the like. The controller 10 realizes the functions according to the embodiment, for example, by reading out and executing a program stored in a storage circuit or a storage device (the storage unit 20 or the like).

The controller 10 includes the display controller 11. The display controller 11 performs control for the display device 2 to display information. The display controller 11 can perform such display control based on information stored in the storage unit 20.

The storage unit 20 stores various information. In the present example, the GUI template 21, the GUI control program 22, and the data processing program 23 are stored in advance in the storage unit 20. The GUI template 21 includes templates of screens, dialogs, icons, and the like displayed as GUIs on the display device 2. The GUI program 22 is a program for the controller 10 to execute control relating to the GUIs displayed based on the GUI template 21. The data processing program 23 is a program for the data processor 40 (and the controller 10) to perform data processing. The operation performed based on these pieces of information will be described later.

The data input and output unit 30 (or, the data I/O unit 30) performs input of data to the ophthalmic image display device 1 and output of data from the ophthalmic image display device 1. It should be noted that the data input and output unit 30 may be configured to only one of input and output data. The data input and output unit 30 may include, for example, a communication device for sending and receiving data via a communication line such as a LAN, the Internet, a dedicated line, or the like. The data input and output unit 30 may include a reader/writer for reading data from a recording medium and writing data to a recording medium. Further, the data input and output unit 30 may include a scanner that reads information recorded on a print medium or the like, a printer that records information on a paper medium, or the like.

The data processor 40 includes a processor that executes the data processing program 23 and performs various kinds of data processing. For example, the data processor 40 applies image processing to image data of the subject's eye. As a typical example thereof, the data processor 40 performs rendering such as three-dimensional computer graphics (3DCG) or the like.

When a three dimensional data set (e.g., volume data, stack data, or the like) acquired through a three dimensional OCT scan (also referred to as a volume scan) of the subject's eye is input to the ophthalmic image display device 1, the data processor 40 is capable of applying various kinds of rendering to the three dimensional data set, thereby forming a B mode image (also referred to as a vertical cross section image, an axial direction cross section image, or the like), a C mode images (also referred to as a transverse cross section image, a horizontal cross section image, or the like), a projection image, a shadowgram, and the like. An image of an arbitrary cross section such as a B mode image or a C mode image is formed through the selection of picture elements (e.g. pixels, voxels, or the like) on a designated cross section from the three dimensional data set. A projection image is formed through the projection of the three dimensional data set in a predetermined direction (e.g., the Z direction, the depth direction, the axial direction, or the like). A shadowgram is formed through the projection of a part of the three dimensional data set (for example, partial data corresponding to a specific layer) in a predetermined direction. An image whose viewpoint is located on the front side of the subject's eye such as a C mode image, a projection image, and a shadowgram is called a front image.

In addition to rendering, the data processor 40 can perform various kinds of image processing. For example, the data processor 40 can perform segmentation for determining a specific tissue or a tissue boundary, and a size analysis for determining the size (e.g., layer thickness, volume, or the like) of a tissue. When a specific layer (or a specific layer boundary) is determined by segmentation, it is possible to reconstruct a B mode image or a front image so that the specific layer becomes flat. Such an image is called a flattened image.

A typical image displayed by the ophthalmic image display device 1 is a blood vessel enhanced image (i.e., an angiogram). The blood vessel enhanced image is an image formed by specifying an image region corresponding to a blood vessel (referred to as a blood vessel region) through analyzing OCT data and changing the expression mode of the blood vessel region to enhance the blood vessel region. For specifying the blood vessel region, a plurality of OCT data acquired through iteratively scanning substantially the same area of the subject's eye is used. In the present embodiment, a three dimensional data set is used to display a blood vessel enhanced image as a planar image (referred to as a blood vessel enhanced front image).

There are several kinds of methods for forming a blood vessel enhanced front image. A typical method for forming a blood vessel enhanced front image will be described. To begin with, by iteratively scanning each of a plurality of B cross sections of the subject's eye, a three dimensional data set that includes a plurality of B mode images arranged in a time series manner for each B cross section is generated. A method for iteratively scanning substantially the same B cross section includes fixation and tracking.

Next, registration of the plurality of B mode images is performed for each B cross section. The registration is performed by using a known image matching technique, for example. As a typical example thereof, extraction of a characteristic region in each B mode image and registration of the plurality of B mode images through position matching of the plurality of characteristic regions extracted can be performed.

Subsequently, a process of specifying image regions that change among the plurality of B mode images after the registration is performed. This process includes, for example, a process of determining the difference between different B mode images. Each B mode image is brightness image data representing the morphology of the subject's eye, and image regions corresponding to sites other than blood vessels are considered to be substantially invariant. On the other hand, taking into consideration that the blood flow randomly varies backscattering that contributes to an interference signal, it is reasonable to presume that an image region varying among the plurality of B mode images after the registration (for example, pixels for which the difference is not zero, or pixels for which the difference is equal to or larger than a predetermined threshold) is a blood vessel region.

To the image region identified in this manner, information indicating that the image region is a blood vessel region is assigned. With this, when displaying a blood vessel enhanced image as a B mode image or a blood vessel enhanced front image, it is possible to change the pixel values of the blood vessel region and highlight the blood vessel region.

The process of forming a blood vessel enhanced image is not limited to this. For example, it is possible to specify a blood vessel region by using the Doppler OCT method as disclosed in the abovementioned Patent Documents 2 to 4, or to specify a blood vessel region by utilizing the image processing as disclosed in the abovementioned Patent Document 5. Also, it is possible to specify a blood vessel region for each site by employing different methods depending on concerned sites. For example, a blood vessel region for the retina may be determined by using the above-described typical method or the Doppler OCT method, and a blood vessel region for the choroid may be determined by using the image processing disclosed in the Patent Document 5.

The functions of the data processor 40 are not limited to the above. For example, the data processor 40 is capable of performing functions appropriately described below and any known functions.

The operation unit 50 is used by the user to input instructions to the ophthalmic image display device 1. The operation unit 50 may include a known operation device used for a computer. For example, the operation unit 50 may include a pointing device such as a mouse, a touch pad, a track ball, or the like. Further, the operation unit 50 may include a keyboard, a pen tablet, a dedicated operation panel, or the like. When the ophthalmic image display device 1 is connected to an ophthalmic apparatus (for example, an OCT apparatus), an instruction may be input to the ophthalmic image display device 1 using an operation device (e.g., a joystick, a button, a switch, or the like) provided in the ophthalmic apparatus. In that case, the operation unit 50 includes such an operation device of the ophthalmic apparatus.

[Display Screen and Usage Mode]

A typical usage mode of the ophthalmic image display device 1 will be described together with examples of the display screens. In the following example, the controller 10 executes the GUI control program 22 to carry out various kinds of processing. In the processing, the GUI template 21 is used as needed. Similarly, the data processor 40 executes the data processing program 23 to carry out various kinds of processing.

First, by iteratively scanning substantially the same area of the subject's eye for each of a plurality of B cross sections, a plurality of two dimensional data sets (e.g., B mode images) arranged in a time series manner is acquired for each B cross section, and a three dimensional data set is generated from the two dimensional data sets. This step is carried out using an ophthalmic OCT apparatus (or a computer processing the data acquired by the ophthalmic OCT apparatus). The ophthalmic OCT apparatus is, for example, installed in the same medical institution as with the ophthalmic image display device 1. The three dimensional data set acquired by the ophthalmic OCT apparatus is transmitted to and stored in an image management server via the LAN constructed in the medical institution, for example. Note that it is possible to execute the formation of a blood vessel enhanced image (e.g., a front image, a B mode image, or the like), segmentation, or the like at the stage before or after storing the three dimensional data set. As another example, the ophthalmic OCT apparatus is installed in a different location from the ophthalmic image display device 1. A three dimensional data set acquired by such an ophthalmic OCT apparatus is transmitted to and stored in an image management server (e.g., a cloud server for image management) via the Internet or a dedicated line, for example. In yet another example, a three dimensional data set acquired by an ophthalmic OCT apparatus is stored in a recording medium. Note that the three dimensional data set is stored and saved in association with the identification information of the concerned patient. The identification information may include, for example, a patient ID given to each patient by a medical institution, public personal identification information (e.g., insurance number, or the like), or the like.

When a user (e.g., a doctor or the like) of the ophthalmic image display device 1 inputs an instruction to start using the GUI, the controller 10 (e.g., the display controller 11) activates the GUI control program 22 and displays a predetermined display screen on the display device 2 based on the GUI template 21. The user inputs patient identification information to the display screen using the operation unit 50. Alternatively, the ophthalmic image display device 1 receives patient identification information through reading a patient card or the like with a card reader included in the data input and output unit 30. The method of entering patient identification information is not limited to the methods described above. Note that in the case where the three dimensional data set stored in the recording medium is input to the ophthalmic image display device 1, the input operation of patient identification information is not necessary.

The controller 10 of the ophthalmic image display device 1 controls the communication device included in the data input and output unit 30 to transmit the input patient identification information to the image management server via the network. The image management server receives the patient identification information, searches for the image data associated with the patient identification information, and transmits the retrieved image data to the ophthalmic image display device 1. At this stage, for example, all or some pieces of image data acquired in the past for the concerned subject's eye (and the fellow eye of the concerned patient) are retrieved and transmitted. For example, it is assumed that the three dimensional data set acquired in the above-described manner is included in this image data. The three dimensional data set may be, for example, a first three dimensional data set in which a plurality of B mode images are assigned to each B cross section, may be a second three dimensional data set obtained by applying the registration, the enhancement processing, and so on to a plurality of B mode images of each B cross section, or may be a third three dimensional data set obtained by voxelizing any of the first three dimensional data set or the second three dimensional data set. In the case where the first three dimensional data set or the third three dimensional data set obtained by voxelizing the first three dimensional data set is used, the registration, the enhancement processing, and so on are carried out by the ophthalmic image display device 1, for example.

The communication device included in the data input and output unit 30 of the ophthalmic image display device 1 receives the image data transmitted from the image management server. The controller 10 stores the received image data together with the patient identification information in the storage unit 20.

The display controller 11 displays a list of pieces of image data of the concerned subject's eye (or of the concerned patient) on the display screen. The user selects desired image data using the operation unit 50. In the present example, it is assumed that the three dimensional data set is selected. The controller 10 reads out the selected three dimensional data set from the storage unit 20 and sends it to the data processor 40.

Figure 2:
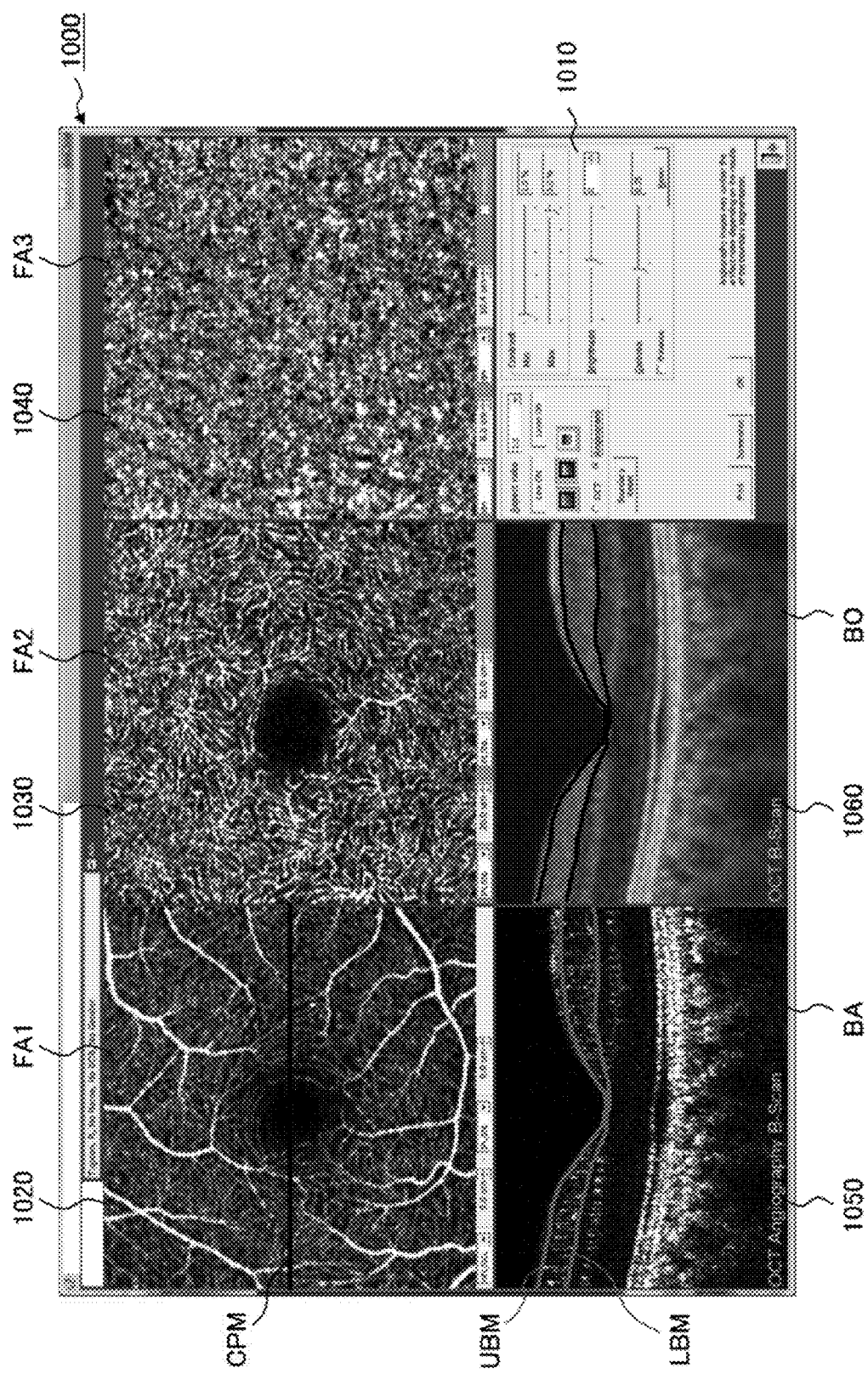
FIG. 2 is a schematic diagram illustrating an example of a screen display of the ophthalmic image display device according to the embodiment.

The display controller 11 displays the summary screen 1000 shown in FIG. 2 based on a summary screen template included in the GUI template 21. The summary screen 1000 is used to observe images of the eye fundus. The summary screen 1000 includes the operation region 1010 provided with software keys for performing various kinds of operations.

In the upper part of the summary screen 1000, three front image display regions 1020, 1030, and 1040 are arranged in parallel in the horizontal direction. The B mode angiogram display region 1050 is arranged below the front image display region 1020 located in the left part of the screen. The B mode image display region 1060 is arranged below the front image display region 1030 located in the central part and arranged on the right side of the B mode angiogram display region 1050. The operation region 1010 is arranged below the front image display region 1040 located in the right part of the screen and arranged on the right side of the B mode image display region 1060.

Between the front image display region 1020 and the B mode angiogram display region 1050, a software key group for performing operations relating to an image displayed on the front image display region 1020 is provided. A similar software key group is also provided between the front image display region 1030 and the B mode image display region 1060 and between the front image display region 1040 and the operation region 1010. Each software key group, in order from the left side, includes the following software keys: a pull-down menu for selecting the kind of a layer (or, of a boundary) of eye fundus that is to be the upper edge of the area to be imaged (i.e., of the slice); an offset display section and an up-down button for moving the position of the upper edge in the depth direction (i.e., the Z direction); a pull-down menu for selecting the kind of a layer (or of a boundary) of eye fundus that is to be the lower edge of the area to be imaged (i.e., of the slice); and an offset display section and an up-down button for moving the position of the lower edge in the depth direction.

Typical examples of options for the upper edges and the lower edges of the slices that can be set using each software key group include ILM (inner limiting membrane), NFL/GCL (nerve fiber layer/ganglion cell layer boundary), IPL/INL (inner plexiform layer/inner nuclear layer boundary), IS/OS (inner segment/outer segment junction), RPE (retinal pigment epithelium), BM (Bruch membrane), CSI (choroid/sclera interface), and the like. The user can set a desired boundary (here, a tissue and a tissue boundary are collectively referred to as a boundary) using each of the upper edge pull-down menu and the lower edge pull-down menu, and furthermore, can set the offset of each of the upper edge and the lower edge by operating the up-down buttons while observing the B mode image or the like. The image region corresponding to each option is specified through the segmentation of the three dimensional data set.

On the right side of the software key group provided between the front image display region 1040 and the operation region 1010, a "Projection" check box is provided for switching the rendering process for forming a front image. When the check box is not checked, the data processor 40 forms a blood vessel enhanced front image using the maximum intensity projection (MIP) process that applies the maximum brightness values in the projection direction, or forms a front OCT image, which is a brightness image, using the averaging process that applies the average of brightness values in the projection direction. On the other hand, when the check box is checked, the data processor 40 forms a front image using the projection process in which the brightness values are integrated in the projection direction for the entire area in the depth direction. By using the "Projection" check box, the user can observe the projection image over the entire depth direction at a desired timing, in the case of both the OCT mode or the angiogram mode. Note that it is also possible to employ a GUI that always displays a projection image. Here, the applicable rendering process is not limited thereto. For example, in a similar manner to the "Projection" check box, a software key for another rendering process can be provided. When such a software key is operated, the data processor 40 executes, for example, any of the following processes: the slab MIP process that applies the MIP process to a slab in the image data; the MinIP process that applies a minimum brightness value in the projection direction; the MPR process that displays an arbitrary cross section; the surface rendering process that displays the surface of an interested site; and the volume rendering process that displays a pseudo three dimensional image of an interested site. The rendered image formed in this manner is displayed on the front image display region 1040 by the display controller 11, for example.

The exemplary operation region 1010 includes the following software keys and the like:

an "Aspect ratio" pull-down menu for setting the aspect ratio of an image to be displayed (e.g., of a B mode image);

a "Layer ON/OFF" button for switching on and off the function of the display of a boundary indicator that indicates the position of a boundary of the fundus over a B mode image;

a "Line ON/OFF" button for switching on and off the function of the display of a cross section position indicator that indicates the position of the cross section of a B mode image over a front image;

a pseudo color display button, a black and white button, and a black and white reversal button for switching the display mode of an image;

an "OCT" mode button and an "Angiogram" mode button for switching the image display mode;

a "Boundary Reset" button for returning the position of the boundary in eye fundus (i.e., the position of the boundary indicator) to the initial position (here, the initial position for macula observation and the initial position for optic disc observation can be set for each of the OCT mode and the angiogram mode);

a "Min" slider and a "Max" slider in the "Contrast" area for adjusting the contrast of an image, as well as a setting value display section (note that the "Min" slider and the "Max" slider are used for contrast adjustment of the B mode image in the OCT mode and for contrast adjustment of the front image in the angiogram);

software keys for numerical value setting and a "Brightness" slider for adjusting the lightness (brightness) of an image;

a setting value display section and a "Gamma" slider for adjusting the gamma value of the image;

an "Enhance" check box for highlighting a specific site;

a "Reset" button used for resetting the setting value of the brightness and the setting value of the gamma value to the respective initial values in the OCT mode, and used for resetting the setting value of the contrast, the setting value of the brightness, and the setting values of the gamma value to the respective initial values in the angiogram mode;

a "Print" button for performing print output;

a "Screenshot" button for taking a screenshot; and an "OK" button for shifting to the detailed observation screen 2000 to be described later.

Note that the operation region 1010 shown in FIG. 2 is an example for the angiogram mode. An example of the operation region 1010 displayed in the OCT mode will be described later.

Figure 3:
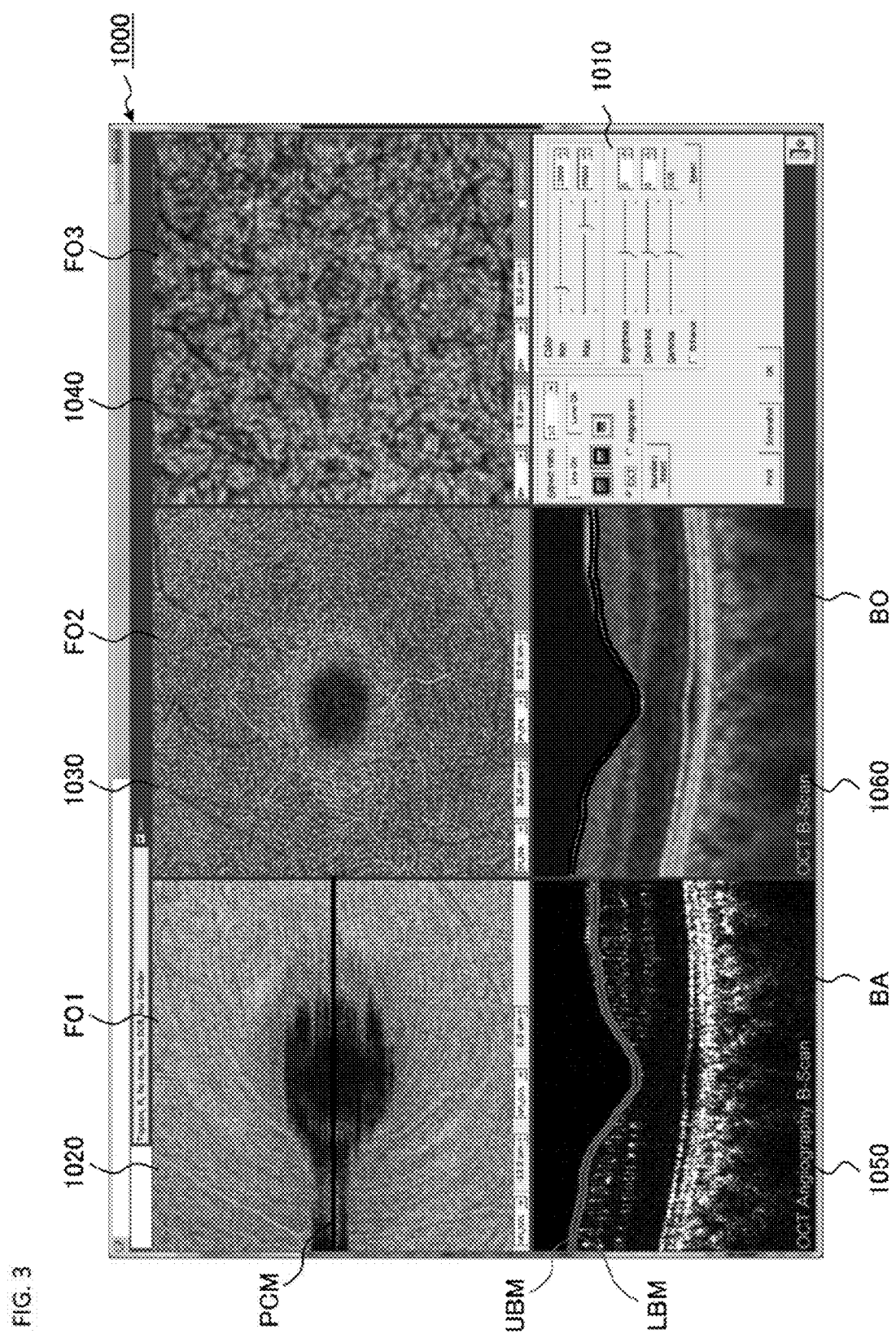
FIG. 3 is a schematic diagram illustrating an example of a screen display of the ophthalmic image display device according to the embodiment.

When the user selects the angiogram mode, the summary screen 1000 on which the images as shown in FIG. 2 are presented is displayed. On the other hand, when the user selects the OCT mode, the summary screen 1000 on which the images as shown in FIG. 3 are presented is displayed. Note that all the images presented in FIG. 2 and FIG. 3 are generated from the same three dimensional data set. The user can observe the state of the blood vessels in the fundus and the morphology of the fundus while switching between the angiogram mode and the OCT mode as needed.

FIG. 2 shows a typical display example of the summary screen 1000 in the angiogram mode. Three blood vessel enhanced front images (also referred to as front angiograms) that represent different sites of the subject's eye from one another are displayed on the front image display regions 1020, 1030, and 1040, respectively. In the display example shown in FIG. 2, the front angiogram FA1 representing the tissues in the area between the NFL/GCL (offset 0) and the IPL/INL (offset 0) is displayed in the front image display region 1020, the front angiogram FA2 representing the tissues in the area between 26.0 μm above the IPL/INL and 52.0 μm below the IPL/INL is displayed in the front image display region 1030, and the front angiogram FA3 representing the tissues in the area between the BM and 10.4 μm below the BM is displayed in the front image display region 1040.

Further, in the display example shown in FIG. 2, the B mode blood vessel enhanced image (also referred to as the B mode angiogram) BA is displayed in the B mode angiogram display region 1050, and the B mode image (also referred to as the B mode OCT image) BO is displayed in the B mode image display region 1060. The B mode angiogram BA and the B mode image BO represent the same cross section.

The cross section position indicator CPM is displayed over the front angiogram FA1 displayed in the front image display region 1020. The cross section position indicator CPM indicates the position in the front angiogram FA1 corresponding to the cross section of the B mode angiogram BA and the B mode image BO. A similar cross section position indicator can also be displayed over the front angiogram(s) FA2 and/or FA3. The opacity (i.e., the α value) of the cross section position indicator CPM is arbitrary.

The boundary indicators UBM and LBM are displayed over the B mode angiogram BA and the B mode image BO. The boundary indicator UBM indicates the position in the B mode angiogram BA corresponding to the upper edge (i.e. the boundary) of the slice of the front angiogram FA1. The boundary indicator LBM indicates the position in the B mode angiogram BA corresponding to the lower edge (i.e., the boundary) of the slice of the front angiogram FA1. Similar boundary indicators are displayed over the B mode image BO. The opacity (i.e., the α values) of the boundary indicators UBM and LBM is arbitrary.

Since the front angiogram FA1 (FA2, FA3), the B mode angiogram BA, and the B mode image BO are images formed from the same three dimensional data set, it is easy to achieve such positional correspondences.

The user can issue an instruction to move the cross section position indicator CPM using the operation unit 50. In response to this operation, the display controller 11 synchronously performs the change in the display position of the cross section position indicator CPM and the update of the display of each of the B mode angiogram BA and the B mode image BO. The operation for moving the cross section position indicator CPM is, for example, a drag operation of the cross section position indicator CPM performed using a mouse. The display controller 11 changes the display position of the cross section position indicator CPM by the movement amount of the drag operation in the movement direction of the drag operation in real time. In parallel with this display control, the data processor 40 respectively forms a B mode angiogram BA and a B mode image BO whose cross sections correspond to a new position of the cross section position indicator CPM, and the display controller 11 displays the newly formed B mode angiogram BA and B mode image BO in the B mode angiogram display region 1050 and the B mode image display region 1060, respectively. Alternatively, these images may be formed in advance and stored in the storage unit 20, and the images may be read out and displayed. As a result, the display of each of the B mode angiogram BA and the B mode image BO is updated.

When the display condition (e.g., the boundary at the upper edge and the boundary at the lower edge) of the front angiogram FA1 is changed using the software key group provided between the front image display region 1020 and the B mode angiogram display region 1050, the display controller 11 displays the boundary indicator UBM at the position corresponding to the boundary at the upper edge after the change, and displays the boundary indicator LBM at the position corresponding to the boundary at the lower edge after the change. Such display control is performed in real time concurrently with the change of the display condition of the front angiogram FA1.

FIG. 3 shows a typical display example of the summary screen 1000 in the OCT mode. In addition to the software keys and the like similar to those in the angiogram mode, the operation region 1010 in the OCT mode includes the "Min" slider and the "Max" slider in the "Color" area for adjusting the color of an image, and the setting value display section.

The front image display regions 1020, 1030, and 1040 display three front images that respectively represent different sites of the subject's eye. In the display example shown in FIG. 3, the front image (i.e., the front OCT image such as a C mode image, a shadowgram, or the like) FO1 representing the tissues in the area from the NFL/GCL (offset is −13.0 μm) to the NFL/GCL (offset 0) is displayed in the front image display region 1020, the front image FO2 representing the tissues in the area between 26.0 μm above the IPL/INL and 52.0 μm below the IPL/INL is displayed in the front image display region 1030, and the front image FO3 representing the tissues in the area between the BM and 52.0 μm below the BM is displayed in the front image display region 1040.

Further, in the display example shown in FIG. 3, in the same manner as in the case of the angiogram mode, the B mode angiogram BA is displayed in the B mode angiogram display region 1050, and the B mode image (i.e., the B mode OCT image) BO is displayed in the B mode image display region 1060. The B mode angiogram BA and the B mode image BO represent the same cross section.

The cross section position indicator CPM is displayed over the front image FO1 displayed in the front image display region 1020. The cross section position indicator CPM indicates the position in the front image FO1 corresponding to the cross section of the B mode angiogram BA and the B mode image BO. A similar cross section position indicator can also be displayed over the front image(s) FO2 and/or FO3. The opacity (i.e., the α value) of the cross section position indicator CPM is arbitrary.

The boundary indicators UBM and LBM are displayed over the B mode angiogram BA and the B mode image BO. The boundary indicator UBM indicates the position in the B mode angiogram BA corresponding to the boundary at the upper edge of the slice of the front image FO1. The boundary indicator LBM indicates the position in the B mode angiogram BA corresponding to the boundary at the lower edge of the slice of the front image FO1. Similar boundary indicators are displayed over the B mode image BO. The opacity (i.e., the α values) of the boundary indicators UBM and LBM is arbitrary.

Since the front image FO1 (FO2, FO3), the B mode angiogram BA, and the B mode image BO are images formed from the same three dimensional data set, it is easy to achieve such positional correspondences.

As in the case of the angiogram mode, the user can issue an instruction to move the cross section position indicator CPM using the operation unit 50. In response to this operation, the display controller 11 synchronously performs the change in the display position of the cross section position indicator CPM and the update of the display of each of the B mode angiogram BA and the B mode image BO. Further, when the display condition (e.g., the boundary at the upper edge and the boundary at the lower edge) of the front image FO1 is changed using the software key group provided between the front image display region 1020 and the B mode angiogram display region 1050, the display controller 11 displays the boundary indicator UBM at the position corresponding to the boundary at the upper edge after the change, and displays the boundary indicator LBM at the position corresponding to the boundary at the lower edge after the change. Such display control is performed in real time concurrently with the change of the display condition of the front image FO1.

Figure 4:
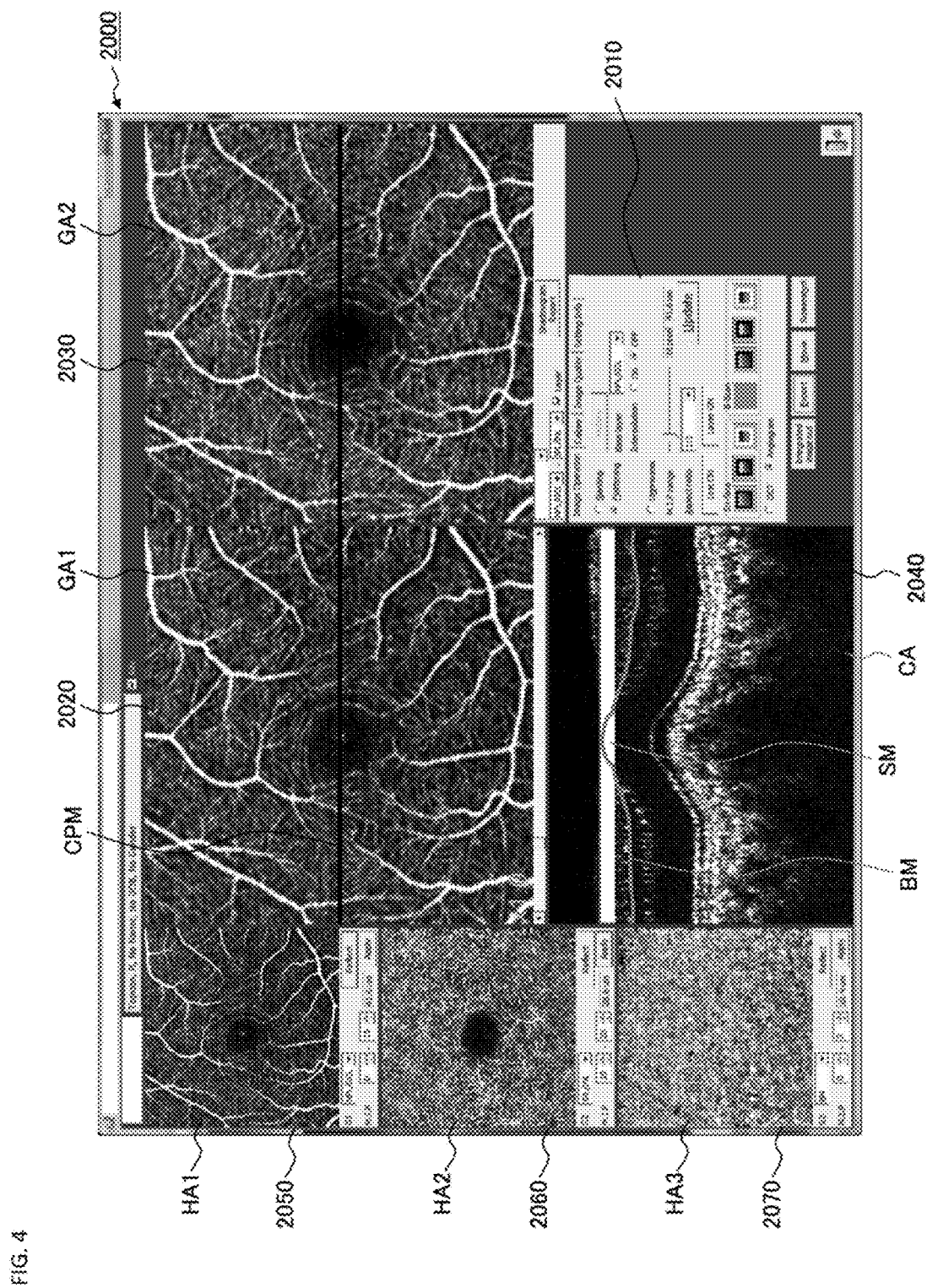
FIG. 4 is a schematic diagram illustrating an example of a screen display of the ophthalmic image display device according to the embodiment.
Figure 5:
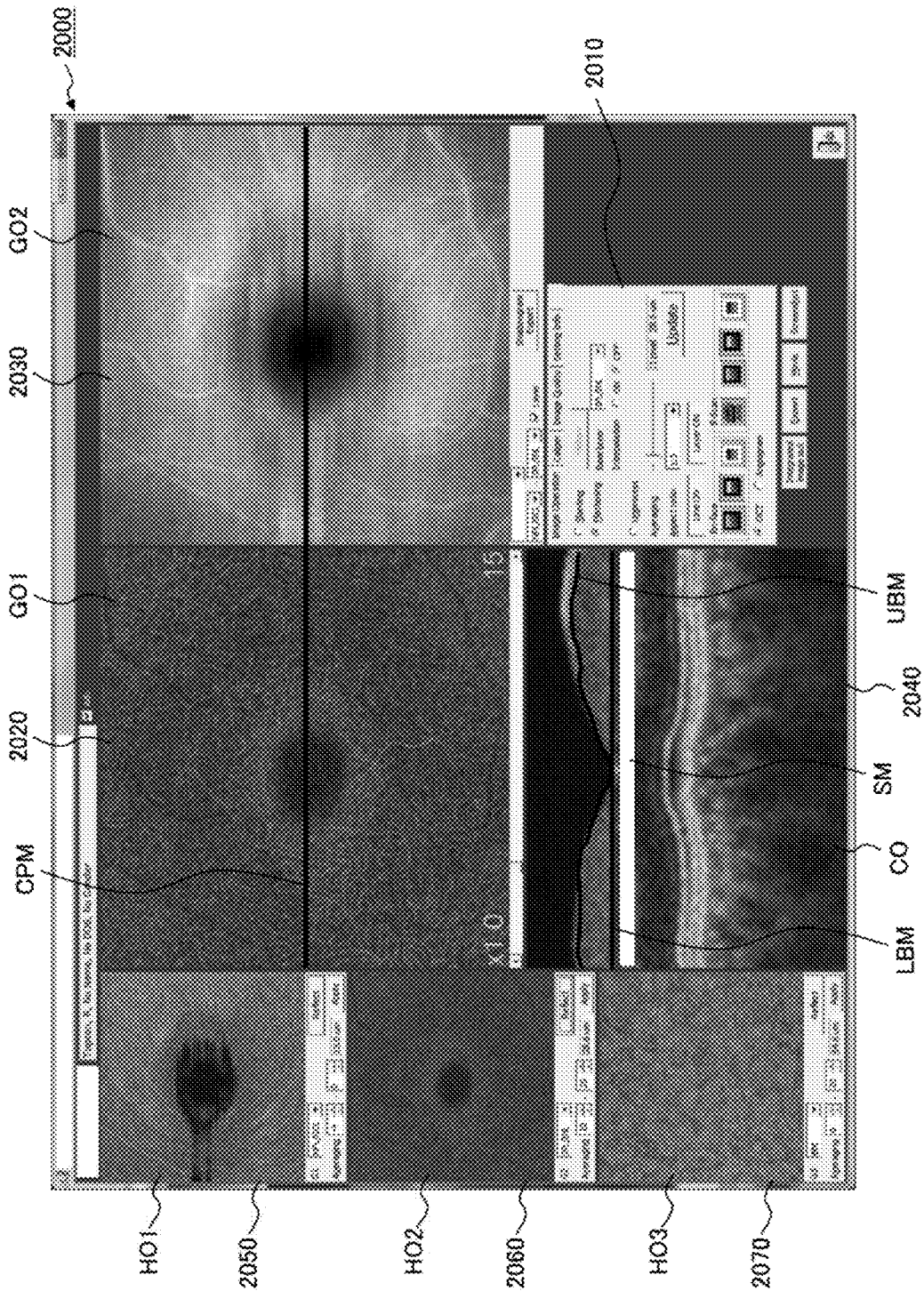
FIG. 5 is a schematic diagram illustrating an example of a screen display of the ophthalmic image display device according to the embodiment.

When the user clicks the "OK" button in the operation region 1010 using the operation unit 50, the display controller 11 shifts from displaying the summary screen 1000 to displaying the detailed observation screen 2000 shown in FIG. 4 or FIG. 5 based on a detailed screen template included in the GUI template 21. The detailed observation screen 2000 shown in FIG. 4 is a screen for the angiogram mode, and the detailed observation screen 2000 shown in FIG. 5 is the screen for the OCT mode. For example, in case where the mode in which the "OK" button in the operation region 1010 on the summary screen 1000 is clicked is the angiogram mode, the display controller 11 displays the detailed observation screen 2000 for the angiogram mode shown in FIG. 4. In case where the mode in which the "OK" button is clicked is the OCT mode, the display controller 11 displays the detailed observation screen 2000 for the OCT mode shown in FIG. 5. The user can observe the state of the blood vessels in the fundus and the morphology of the fundus while switching between the angiogram mode and the OCT mode as needed.

The detailed observation screen 2000 includes the operation region 2010 provided with software keys for performing various kinds of operations. The operation region 2010 includes the following four tabs that are used for switching operation modes:

an "Image Operation" tab for performing an operation on an image;

a "Caliper" tab for performing various kinds of measurements;

an "Image Quality" tab for adjusting image quality; and a "Setting Info" tab to present setting information.

When the user clicks a tab corresponding to a desired operation mode using the operation unit 50, the display controller 11 displays an operation screen corresponding to the clicked tab in the operation region 2010.

In the detailed observation screen 2000 for the angiogram mode shown in FIG. 4, the "Image Operation" tab has been selected. In this case, the following software keys and the like are provided in the operation region 2010:

a "Slanting" check box for switching the state of the orientation of a slice between fixed and variable (when the check box is checked, the orientation of the slice can be changed as one likes);

a "History" button for presenting the history of the settings of the positions and orientations of slices;

a "Base Layer" pull-down menu for setting a reference boundary (also referred to as a base layer);

a "Flattening" check box for applying the flattening processing to a B mode image so that the base layer set using the "Base Layer" pulldown menu becomes flat (when the check box is checked, the flattening processing is applied to the displayed B mode image (e.g., the B Mode angiogram CA or the like));

an "Interpolation ON/OFF" check box for switching on and off the application of the interpolation processing to a display image or to the three dimensional data set;

a setting value display section and an "MIP range" slider for setting an imaging area (i.e., a slice) to which the MIP process is to be applied for the purpose of forming a front image (here, a slice thickness can be set on a pixel-to-pixel basis with the designated depth position as the center);

an "Aspect ratio" pull-down menu for setting the aspect ratio of an image to be displayed (for example, of a B mode image);

an "Update" button for updating the display with an image to which the current setting has been applied;

a "Layer ON/OFF" button for switching on and off the function of displaying a boundary indicator that indicates the position of a boundary of the fundus over a B mode image;

a "Line ON/OFF" button for switching on and off the function of displaying a cross section position indicator that indicates the position of the cross section of a B mode image over a front image;

a pseudo color display button, a black and white button, and a black and white reversal button arranged within the "En-face" frame for switching the display mode of a front image;

a pseudo color display button, a black and white button, and a black and white reversal button arranged within the "B-Scan" frame for switching the display mode of a B mode image;

an "OCT" mode button and an "Angiogram" mode button for switching the image display mode;

an "Integrated image out" button for outputting an integrated image;

an "Export" button for exporting an image, information, or the like displayed on the detailed observation screen 2000;

a "Movie" button for saving a moving image; and a "Screenshot" button for taking a screenshot.

The configuration of the operation region 2010 when another tab has been selected will be described later.

Instead of the "MIP range" slider and the setting value display section, the operation region 2010 for the OCT mode shown in FIG. 5 includes an "Averaging" slider and a setting value display section for setting an imaging area (i.e., a slice) to which the averaging process is to be applied for the purpose of forming a front image (here, a slice thickness can be set on a pixel-to-pixel basis with the designated depth position as the center).

At least part of the setting contents in the summary screen 1000 at the time when the "OK" button in the operation region 1010 on the summary screen 1000 is clicked can be reflected to the initial setting in the operation region 2010. Examples of settings of the detailed observation screen 2000 to which settings of the summary screen 1000 are reflected include the followings: the setting of the "Aspect ratio" pull-down menu; the setting of the "Layer ON/OFF" button; the setting of the "Line ON/OFF" button; the setting of the pseudo color display button, the black and white button, and the black and white reversal button provided within the "En-face" frame; the setting of the pseudo color display button, the black and white button, and the black and white reversal button provided within the "B-Scan" frame; and the setting of the "OCT" mode button and the "Angiogram" mode button.

The layout and the like of the detailed observation screen 2000 for the angiogram mode shown in FIG. 4 will be described. The front image display region 2020 is provided at the center upper part of the detailed observation screen 2000, and the front image display region 2030 is also provided on the right side of the front image display region 2020. The B mode image display region 2040 is arranged below the front image display region 2020. The operation region 2010 is arranged below the front image display region 2030 and to the right side of the B mode image display region 2040.

In the front image display regions 2020 and 2030, two front angiograms GA1 and GA2 each representing different sites of the subject's eye from one another are displayed respectively. In the display example shown in FIG. 4, the front angiogram GA1 formed by applying the MIP process on the slice that has been set using the "MIP range" slider in the operation region 2010 is displayed in the front image display region 2020. Further, the display controller 11 displays the slice indicator SM indicating the area of the slice that has been set using the "MIP range" slider over the B mode image (e.g., the B mode angiogram CA) displayed in the B mode image display region 2040.

Between the front image display region 2030 and the operation region 2010, a software key group is provided for performing operations relating to an image displayed on the front image display region 2030. The software key group includes two pull-down menus for selecting the kinds of boundaries to be both edges of the slice. The options for the boundaries in the pull-down menus are, for example, ILM, NFL/GCL, IPL/INL, IS/OS, RPE, BM, CSI, and the like as in the case of the summary screen 1000. When the user sets a desired boundary in each of the pull-down menus, the data processor 40 specifies two set boundaries from the result of segmentation of the three dimensional data set, and performs the MIP process or the averaging process on the image region sandwiched between the two boundaries to form a front image. The display controller 11 displays the formed front image in the front image display region 2030. A "Shadowgram Export" button for exporting a shadowgram is provided on the right side of the pull-down menus.

Further, in the left edge portion of the detailed observation screen 2000, three image setting regions 2050, 2060, and 2070 for carrying out various kinds of settings relating to a front image are provided. Each of the image setting regions 2050 to 2070 includes a region in which a front image is displayed and a software key group for performing the setting relating to the front image displayed on the region. The front image displayed in each of the image setting regions 2050 to 2070 is a front angiogram in the angiogram mode and a front OCT image (e.g., a C mode image, a shadowgram, a projection image, or the like) in the OCT mode.

In the display example of the angiogram mode shown in FIG. 4, the front angiogram HA1 is displayed in the image setting region 2050, the front angiogram HA2 is displayed in the image setting region 2060, and the front angiogram HA3 is displayed in the image setting region 2070. It should be noted that when shifting to the detailed observation screen 2000, the front image(s) displayed in at least one of the front image display regions 1020 to 1040 in the summary screen 1000 may be displayed in the image setting region 2060, and the setting for the front image(s) may be reflected to the software key group in the image setting region 2060.

In addition, the software key group for each image setting region 2050 to 2070 includes software keys and the like as the followings:

a pull-down menu for setting a base boundary (i.e., base layer) (the options of the pull-down menu include ILM, NFL/GCL, IPL/INL, IS/OS, RPE, BM, CSI, and so on, for example);

a software key for numerical value setting and a slice thickness display section for setting a slice on which the MIP process is to be performed for the purpose of forming a front image to be displayed in the concerned image setting region (2050, 2060 or 2070) (these software keys are used for setting the upper offset and the lower offset corresponding to the base layer. The slice thickness set with the software keys is converted into the unit μm and displayed in the slice thickness display section);

an "Apply" button for displaying the front image formed by the MIP process, in which the slice set by the aforementioned software key group is applied, in the concerned image setting region;

a "Reflect" button for displaying the front image displayed in the concerned image setting region in the front image display region 2020.

When the "Apply" button is clicked, the data processor 40 forms a new front angiogram by applying the MIP process to the slice that has been set by the software key group (i.e., to a part of the three dimensional data set). The display controller 11 displays the new front angiogram in the concerned image setting region. As a result, the display of the front angiogram displayed in the image setting region is updated.

Further, when the "Apply" button is clicked, the controller 10 can store the settings of the slice (e.g., the position of the slice in the three dimensional data set) in the storage unit 20. At this time, the controller 10 can store the settings of the slice in association with the three dimensional data set. In addition, it is also possible to associate the settings of the slice with arbitrary information such as the setting date and time of the slice and the information (e.g., image data or the like) referred to in parallel. After completion of the current diagnostic imaging (e.g., the interpretation of images), when the detailed observation screen 2000 is activated again for observing the concerned subject's eye, the following processing may be performed. First, the controller 10 reads out the settings of the slice from the storage unit 20 and sends them to the data processor 40. The data processor 40 applies the MIP process to the three dimensional data set associated with the settings of the slice or to a newly acquired three dimensional data set, based on the settings of the slice read out. The display controller 11 displays the front angiogram formed in this manner in the image setting region. Through such processing, it becomes possible to re-display a front angiogram displayed in the past, and to re-apply a setting of a slice applied in the past to construct a new front angiogram.

When the "Reflect" button is clicked, the display controller 11 replaces the front angiogram GA1 displayed in the front image display region 2020 with a front angiogram (for example, the front angiogram HA1) displayed in the concerned image setting region (that is, the image displayed in the front image display region 2020 is updated to a new front angiogram GA1). At the same time, the display controller 11 reflects the settings of the new front angiogram GA1 (for example, the front angiogram HA1) to the B mode angiogram CA displayed in the B mode image display region 2040 and the operation region 2010. For example, the display controller 11 can display the slice indicator SM that indicates the slice set using the software key group over the B mode angiogram CA, and can reflect the setting contents set using the software key group to the "MIP range" slider or the like in the operation region 2010.

The cross section position indicator CPM is displayed over the front angiogram GA1 displayed in the front image display region 2020. The cross section position indicator CPM indicates the position in the front angiogram GA1 corresponding to the cross section of the B mode angiogram CA. A similar cross section position indicator can also be displayed over the front angiogram GA2. The opacity (i.e., the α value) of the cross section position indicator CPM is arbitrary.

In addition, as described above, the slice indicator SM of a band-like shape is displayed over the B mode angiogram CA. The slice indicator SM indicates the position in the B mode angiogram CA corresponding to the slice of the front angiogram GA1. The opacity (i.e., the α value) of the slice indicator SM is arbitrary. Further, the boundary indicator BM, which indicates the position in the B mode angiogram CA corresponding to the boundary set by using the software key group provided between the operation region 2010 and the front image display region 2030, is displayed over the B mode angiogram CA.

Since the front angiogram GA1 and the B mode angiogram CA are images formed from the same three dimensional data set, it is easy to achieve such positional correspondence for displaying the slice indicator SM.

The user can issue an instruction to move the cross section position indicator CPM using the operation unit 50. In response to this operation, the display controller 11 synchronously performs the change in the display position of the cross section position indicator CPM and the update of the display of the B mode angiogram CA. The operation for moving the cross section position indicator CPM is, for example, a drag operation of the cross section position indicator CPM performed using a mouse. The display controller 11 changes the display position of the cross section position indicator CPM by the movement amount of the drag operation in the movement direction of the drag operation in real time. In parallel with this display control, the data processor 40 forms a B mode angiogram CA whose cross section corresponds to a new position of the cross section position indicator CPM, and the display controller 11 displays the newly formed B mode angiogram CA in the B mode image display region 2040. Alternatively, this image may be formed in advance and stored in the storage unit 20, and the image may be read out and displayed. As a result, the display of the B mode angiogram CA is updated.

In addition, the user can issue an instruction to move the slice indicator SM using the operation unit 50. In response to this operation, the display controller 11 synchronously performs the change in the display position of the slice indicator SM and the update of the display of the front angiogram GA1. The operation for moving the slice indicator SM is, for example, a drag operation of the slice indicator SM performed using a mouse. The display controller 11 changes the display position of the slice indicator SM by the movement amount of the drag operation in the movement direction of the drag operation in real time. In parallel with this display control, the data processor 40 forms a front angiogram GA1 whose slice corresponds to a new area indicated by the slice indicator SM, and the display controller 11 displays the newly formed front angiogram GA1 in the front image display region 2020. As a result, the display of the front angiogram GA1 is updated.

When the "Slanting" check box is checked, it is possible to change the orientation of the slice indicator SM. When the user performs an operation for changing the orientation of the slice indicator SM using the operation unit 50, the display controller 11, in response to this operation, synchronously performs the change in the display position (i.e., the orientation) of the slice indicator SM and the update of the display of the front angiogram GA1. The operation for moving the slice indicator SM is, for example, a drag operation of the slice indicator SM. The display controller 11 rotates the display position of the slice indicator SM by the movement angle of the drag operation in the movement direction of the drag operation in real time. In parallel with this display control, the data processor 40 forms a front angiogram GA1 whose slice corresponds to a new area indicated by the slice indicator SM, and the display controller 11 displays the newly formed front angiogram GA1 in the front image display region 2020. As a result, the display of the front angiogram GA1 is updated.

It is also possible to configure so that the slice thickness can be changed by, for example, dragging the upper edge and/or the lower edge of the slice indicator SM in addition to the movement of the slice indicator SM in a state in which the slice thickness is maintained. Also in this case, the display control of the slice indicator SM and the update of the display of the front angiogram GA1 can be performed synchronously.

The detailed observation screen 2000 in the OCT mode shown in FIG. 5 will be described. Unless otherwise mentioned, the configuration of the detailed observation screen 2000 for the OCT mode and data processing and control relating thereto are the same as those in the case of the angiogram mode.

In the detailed observation screen 2000 for the OCT mode, the display regions of images and the layout of the software keys are the same as those in the case of the angiogram mode. In the front image display regions 2020 and 2030, two front images (e.g., front OCT images such as a C mode image, a shadowgram, or the like) GO1 and GO2 each representing different sites of the subject's eye are displayed, respectively. In the display example shown in FIG. 5, the front image GO1, which is formed by projecting a slice that has been set using the "Averaging" slider in the operation region 2010, is displayed in the front image display region 2020. Further, the display controller 11 displays the slice indicator SM indicating the area of the slice that has been set using the "Averaging" slider over the B mode image (e.g., the B mode OCT image CO) displayed in the B mode image display region 2040.

As in the case of the angiogram mode, a software key group is provided between the front image display region 2030 and the operation region 2010 for performing operations relating to images displayed in the front image display region 2030. When the user sets a desired boundary using each of the pull-down menus, the data processor 40 specifies two boundaries having been set from the result of segmentation of the three dimensional data set, and executes the averaging process (or the projection process) on the image region sandwiched between these boundaries to form a front image. The display controller 11 displays the formed front image in the front image display region 2030.

In each of the three image setting regions 2050, 2060, and 2070 provided in the left edge portion of the detailed observation screen 2000, a region in which a front image is displayed and a software key group for performing settings relating to the front image displayed in this region are provided. The front image H01 is displayed in the image setting region 2050, the front image H02 is displayed in the image setting region 2060, and the front image H03 is displayed in the image setting region 2070.

In addition, the software key group for each of the image setting regions 2050 to 2070 includes software keys and the like as the followings:

a pull-down menu for setting the base layer;

a software key for numerical value setting and a slice thickness display section for setting a slice to which the projection process is to be applied for the purpose of forming a front image to be displayed in the concerned image setting region (2050, 2060 or 2070);

an "Apply" button for displaying the front image formed by the projection process applied to the slice set by the aforementioned software key group in the concerned image setting region; and a "Reflect" button for displaying the front image displayed in the concerned image setting region in the front image display region 2020.

When the "Apply" button is clicked, the data processor 40 forms a new front image by applying the projection process to the slice that has been set using the software key group (i.e., a part of the three dimensional data set). The display controller 11 displays this new front image in the concerned image setting region. As a result, the display of the front image displayed in the concerned image setting region is updated.

Further, when the "Apply" button is clicked, the controller 10 can store the settings of the slice (e.g., the position of the slice in the three dimensional data set) in the storage unit 20. At this time, the controller 10 can associate the settings of the slice with arbitrary information such as the three dimensional data set, the setting date and time of the slice, the information (e.g., image data or the like) referred to in parallel. As a result, as in the case of the angiogram mode, it becomes possible to re-display a front image displayed in the past, and to re-apply a setting of a slice applied in the past to construct a new front image.

When the "Reflect" button is clicked, the display controller 11 replaces the front image GO1 displayed in the front image display region 2020 with the front image HO (for example, the front image HO1) displayed in the concerned image setting region. At the same time, the display controller 11 reflects the settings of the new front image GO1 (for example, the front image HO1) to the B mode image CO displayed in the B mode image display region 2040 and the operation region 2010. For example, the display controller 11 can display the slice indicator SM that indicates the slice set using the software key group over the B mode image CO, and can reflect the setting contents set using the software key group to the "Averaging" slider or the like in the operation region 2010.

The cross section position indicator CPM is displayed over the front image GO1 displayed in the front image display region 2020. The cross section position indicator CPM indicates the position in the front image GO1 corresponding to the cross section of the B mode image CO. A similar cross section position indicator can also be displayed over the front image GO2. The opacity (i.e., the α value) of the cross section position indicator CPM is arbitrary.

In addition, as described above, the slice indicator SM of a band-like shape is displayed over the B mode image CO. The slice indicator SM indicates the position in the B mode image CO corresponding to the slice of the front image GO1. The opacity (i.e., the α value) of the slice indicator SM is arbitrary. Furthermore, the boundary indicators UBM and LBM are displayed over the B mode image CO. The boundary indicator UBM indicates the position in the B mode image CO corresponding to the boundary at the upper edge of the slice of the front image GO1. The boundary indicator LBM indicates the position in the B mode image CO corresponding to the boundary at the lower edge of the slice of the front image GO1.

Since the front image GO1 and the B mode image CO are images formed from the same three dimensional data set, it is easy to achieve such positional correspondence for displaying the slice indicator SM.

The user can issue an instruction to move the cross section position indicator CPM using the operation unit 50. In response to this operation, the display controller 11 synchronously performs the change in the display position of the cross section position indicator CPM and the update of the display of the B mode image CO. The operation for moving the cross section position indicator CPM is, for example, a drag operation of the cross section position indicator CPM performed using a mouse. The display controller 11 changes the display position of the cross section position indicator CPM by the movement amount of the drag operation in the movement direction of the drag operation in real time. In parallel with this display control, the data processor 40 forms a B mode image CO whose cross section corresponds to a new position of the cross section position indicator CPM, and the display controller 11 displays the newly formed B mode image CO in the B mode image display region 2040. As a result, the display of the B mode image CO is updated.

In addition, the user can issue an instruction to move the slice indicator SM using the operation unit 50. In response to this operation, the display controller 11 synchronously performs the change in the display position of the slice indicator SM and the update of the display of the front image GO1. The operation for moving the slice indicator SM is, for example, a drag operation of the slice indicator SM performed using a mouse. The display controller 11 changes the display position of the slice indicator SM by the movement amount of the drag operation in the movement direction of the drag operation in real time. In parallel with this display control, the data processor 40 forms a front image GO1 whose slice corresponds to a new area indicated by the slice indicator SM, and the display controller 11 displays the newly formed front image GO1 in the front image display region 2020. As a result, the display of the front image GO1 is updated.

When the "Slanting" check box is checked, it is possible to change the orientation of the slice indicator SM. When the user performs an operation for changing the orientation of the slice indicator SM using the operation unit 50, the display controller 11, in response to this operation, synchronously performs the change in the display position (i.e., the orientation) of the slice indicator SM and the update of the display of the front image GO1. The operation for moving the slice indicator SM is, for example, a drag operation of the slice indicator SM. The display controller 11 rotates the display position of the slice indicator SM by the movement angle of the drag operation in the movement direction of the drag operation in real time. In parallel with this display control, the data processor 40 forms a front image GO 1 whose slice corresponds to a new area indicated by the slice indicator SM, and the display controller 11 displays the newly formed front image GO1 in the front image display region 2020. As a result, the display of the front image GO1 is updated.

It is also possible to configure so that the slice thickness can be changed by, for example, dragging the upper edge and/or the lower edge of the slice indicator SM in addition to the movement of the slice indicator SM in a state in which the slice thickness is maintained. Also in this case, the display control of the slice indicator SM and the update of the display of the front image GO1 can be performed synchronously.

As described above, four tabs are provided in the upper part of the operation region 2010. Specifically, these tabs include the followings: an "Image Operation" tab for performing an operation on an image; a "Caliper" tab for performing various kinds of measurements; an "Image Quality" tab for adjusting the image quality; and a "Setting Info" tab for presenting the setting information. The configuration of the operation region 2010 when the "Image Operation" tab is selected and the operation, control and data processing relating thereto have been described above with reference to FIG. 4 and FIG. 5. Hereinafter, the configuration of the operation region 2010 when another tab is selected, and the operation, control, and data processing relating thereto will be described.

The following drawings (i.e., FIG. 6 to FIG. 8) are examples of the screens displayed when another tab is clicked in the detailed observation screen 2000 for the angiogram mode shown in FIG. 4 (in which case, the "Image Operation" tab has been selected). Descriptions of parts other than the operation region 2010 will be omitted.

Figure 6:
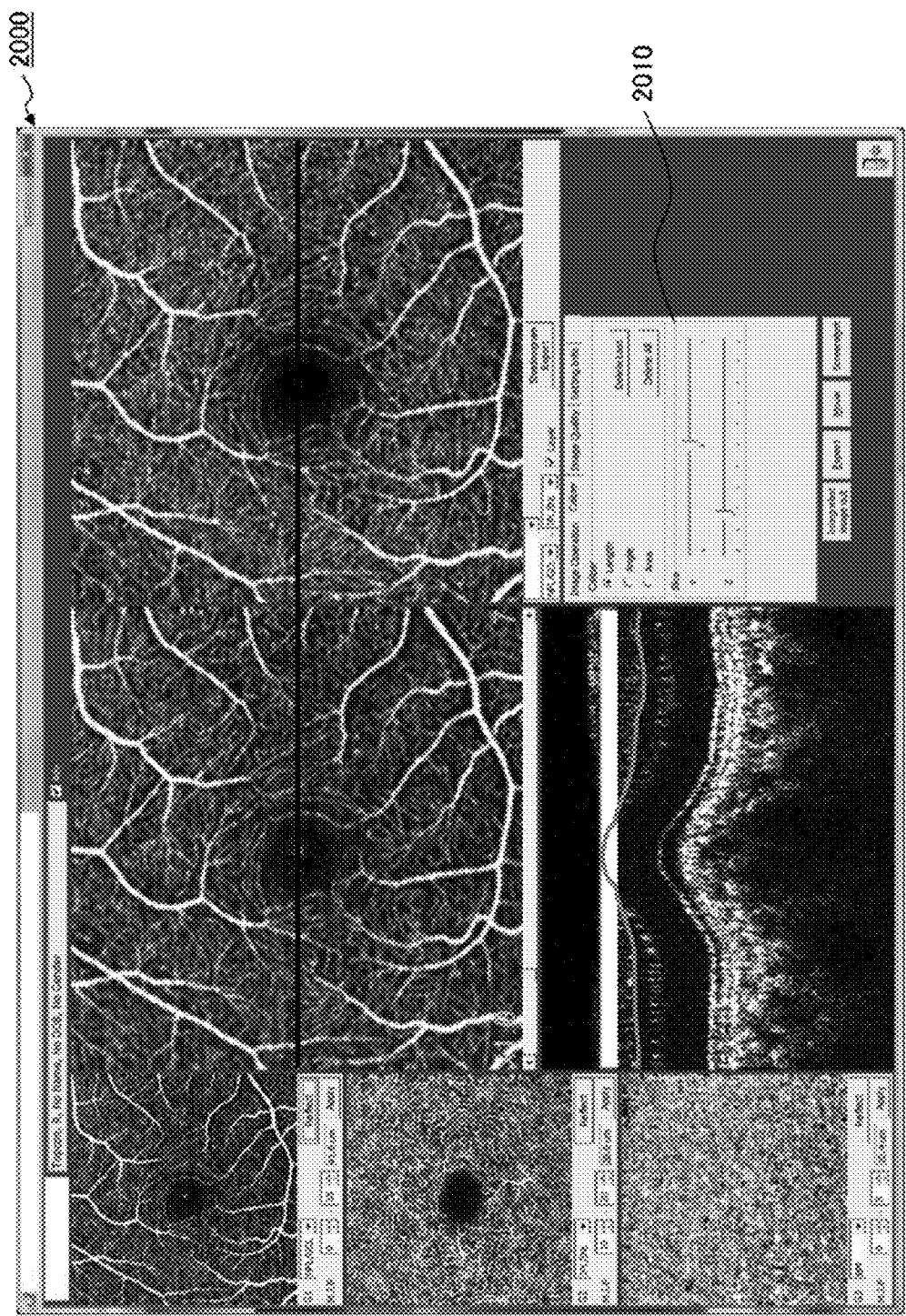
FIG. 6 is a schematic diagram illustrating an example of a screen display of the ophthalmic image display device according to the embodiment.

FIG. 6 shows the detailed observation screen 2000 when the "Caliper" tab has been selected. The "Caliper" function is used to measure a site depicted in the images displayed in the front image display region 2020 and the B mode image display region 2040. In the operation region 2010 in the detailed observation screen 2000, the following software keys and the like are provided:

a "Length" check box for measuring a length;

an "Angle" check box for measuring an angle;

an "Area" check box for measuring an area (i.e., a square measure);

a "Delete Last" button for deleting the result of the latest measurement;

a "Delete All" button for deleting the results of all the measurements having been performed;

a "Slice Y" slider for moving the cross section position indicator CPM displayed in the front image display region 2020 in the vertical direction (i.e., the Y direction);

a "Slice Z" slider for moving the slice indicator SM displayed in the B mode image display region 2040 in the depth direction (i.e., the Z direction);

an "Integrated image out" button for outputting an integrated image;

an "Export" button for exporting an image and information displayed on the detailed observation screen 2000;

a "Movie" button for saving a moving image; and a "Screenshot" button for taking a screenshot.

When a check is input to the "Length" check box, the display controller 11 displays a length measurement indicator (i.e., a gauge) for performing length measurement over a display image (e.g., a front image, a B mode image, or the like), for example. The length measurement indicator is, for example, an image of a line-segment shape. The user can change the position and the length (e.g., the positions of the end points) of the length measurement indicator using the operation unit 50. When the user places the length measurement indicator at a desired position in the display image, the data processor 40 determines the actual size (e.g., in the unit μm, mm, or the like) corresponding to the length of the length measurement indicator at that time. The controller 10 stores the actual size data obtained by the data processor 40 in the storage unit 20 in association with the position in the display image where the length measurement indicator (e.g., the both ends of the length measurement indicator) is placed.

The interface for measuring the length is not limited to this. For example, it is possible to configure so that the location in which the length is to be measured is designated by the user clicking on two desired points in the display image. In addition to measuring the linear distance between two points, it is also possible to measure the length along a predetermined curve or curved surface. For example, it can be configured to measure the length along a predetermined layer, boundary, blood vessel or lesion.

When a check is input to the "Angle" check box, the display controller 11 displays an angle measurement indicator (i.e., a gauge) for performing angle measurement over a display image (e.g., a front image, a B mode image, or the like), for example. The angle measurement indicator is, for example, an image that has a shape excluding one side from an equilateral triangle. Using the operation unit 50, the user can change the position of the angle measurement indicator and the angle formed by the two sides that form the angle measurement indicator. The user places the angle measurement indicator at a desired position in the display image and adjusts the angle formed by the two sides that form the angle measurement indicator according to the shape of the depicted tissue. The data processor 40 determines the angle formed by the two sides that form the angle measurement indicator. The controller 10 stores the angle data obtained by the data processor 40 in the storage unit 20 in association with the position in the display image where the angle measurement indicator (e.g., the two sides that form the angle measurement indicator) is placed.

The interface for measuring the angle is not limited to this. For example, it is possible to designate the location to measure an angle by the user clicking on three desired points in the display image, or drawing two line segments on the display image. It is also possible to configure not only to measure the angle on a plane but also to measure the solid angle.

When a check is input to the "Area" check box, the display controller 11 displays, for example, an area measurement indicator (i.e., a gauge) for performing area measurement over the display image (e.g., a front image, a B mode image, or the like). The area measurement indicator is, for example, an image of an arbitrary two dimensional shape. Using the operation unit 50, the user can change the position, shape, size, or the like of the area measurement indicator (e.g., the location of the outline of the area measurement indicator). When the user places the area measurement indicator at a desired position in the display image, the data processor 40 determines the actual size (e.g., in the unit $\mu m^2$, $mm^2$, or the like) corresponding to the shape, size, or the like of the area measurement indicator at that time. The controller 10 stores the actual size data obtained by the data processor 40 in the storage unit 20 in association with the position in the display image where the area measurement indicator is placed. The interface for measuring the area (i.e., the square measure) is not limited to this. It is also possible to configure so that the volume (i.e., the cubic volume) can be measured.

Figure 7:
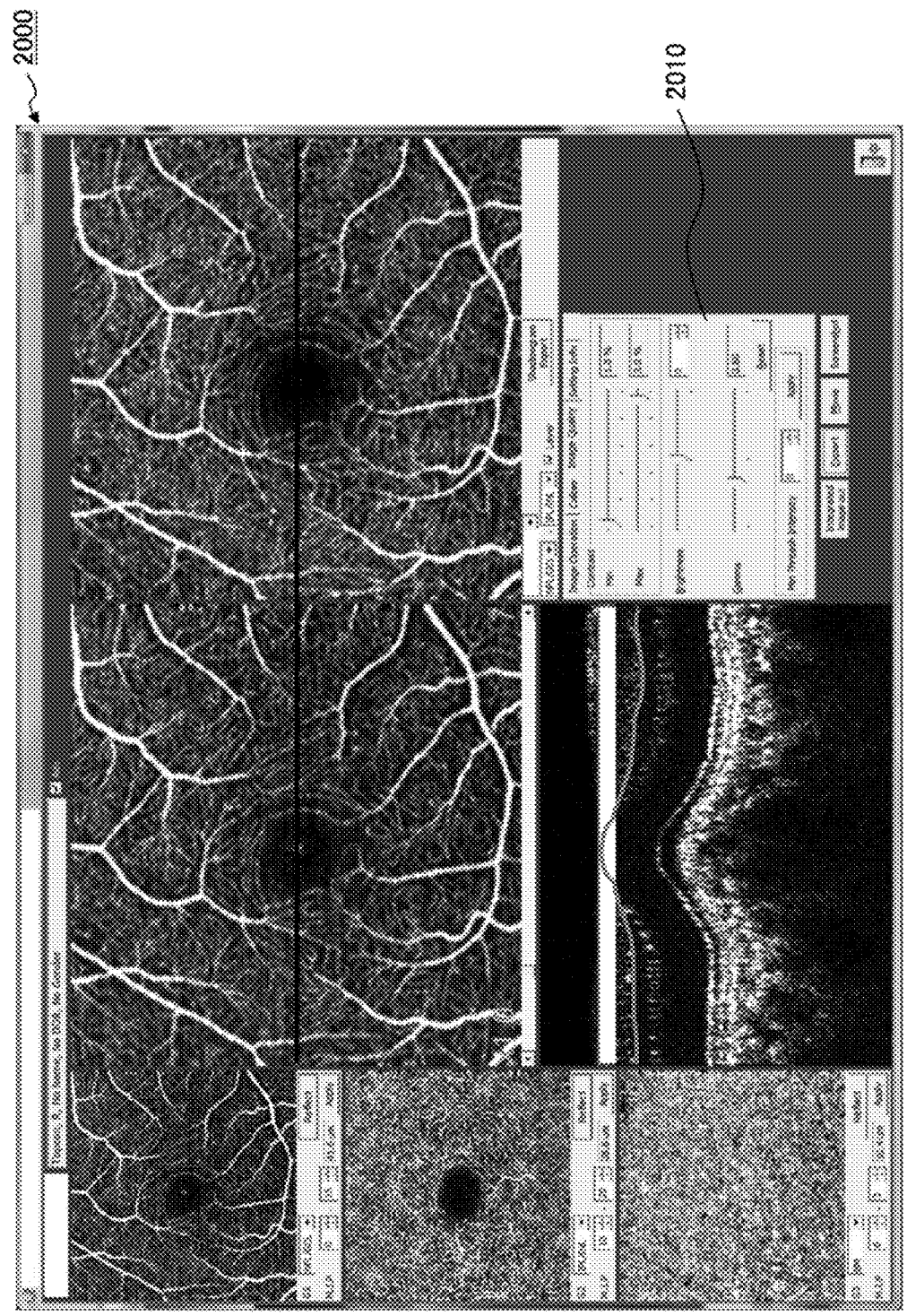
FIG. 7 is a schematic diagram illustrating an example of a screen display of the ophthalmic image display device according to the embodiment.

FIG. 7 shows the detailed observation screen 2000 when the "Image Quality" tab has been selected. In the operation region 2010 on this detailed observation screen 2000, the following software keys and the like are provided:

a "Min" slider and a "Max" slider in the "Contrast" area for adjusting the contrast of an image, and a setting value display section;

software keys for numerical value setting and a "Brightness" slider for adjusting the lightness (brightness) of an image;

a "Reset" button for resetting a setting value by the software keys to the initial value;

a "Min Thresh Intensity" software key for setting a threshold value of the minimum intensity, and an "Apply" button for applying the setting thereof;

an "Integrated image out" button for outputting an integrated image;

an "Export" button for exporting an image and information displayed on the detailed observation screen 2000;

a "Movie" button for saving a moving image; and a "Screenshot" button for taking a screenshot.

Figure 8:
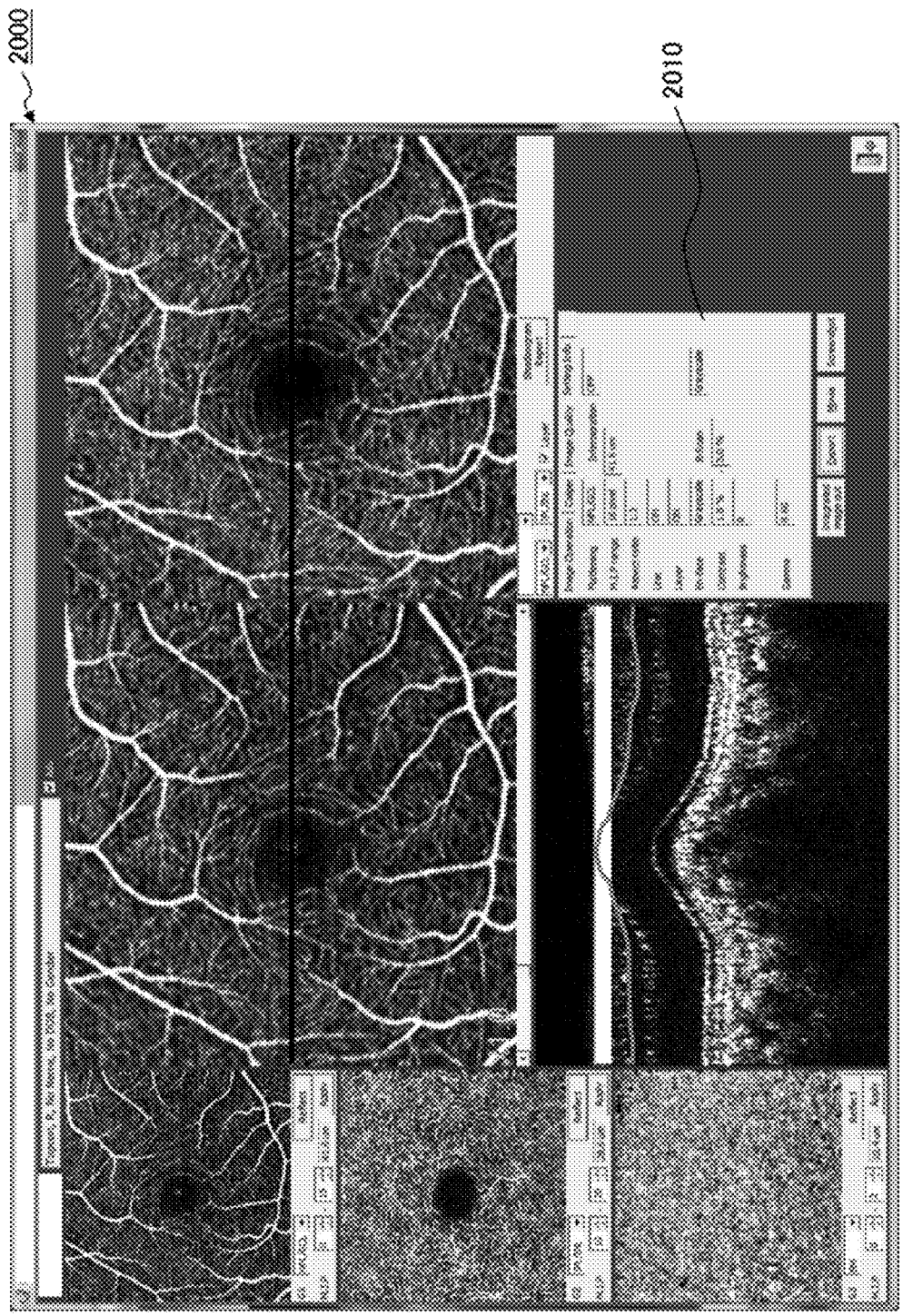
FIG. 8 is a schematic diagram illustrating an example of a screen display of the ophthalmic image display device according to the embodiment.

FIG. 8 shows the detailed observation screen 2000 when the "Setting Info" tab has been selected. Various kinds of information display sections are provided in the operation region 2010 in the detailed observation screen 2000, and the current setting values and setting states are presented.

[Actions and Effects]

The actions and effects of the ophthalmic image display device according to the embodiment will be described.

The ophthalmic image display device (1) of the embodiment includes at least a display controller (11) for displaying information on a display means (the display device 2) and an operation unit (50).

The display controller (11) displays, in a predetermined layout (summary screen 1000), a B mode image (BO), a blood vessel enhanced image (BA) representing the same cross section as the B mode image (BO), and one or more front images (FA1 to FA3, or FO1 to FO3) individually formed based on a three dimensional data set (e.g., volume data, stack data, or the like) acquired by performing OCT on a subject's eye. Here, the meaning of "based on a three dimensional data set" includes both "based on an entire three dimensional data set" and "based on part of a three dimensional data set". In addition, the three dimensional data set is formed, for example, by scanning each of a plurality of B cross sections a predetermined number of times, forming a predetermined number of B mode images for each of the plurality of B cross sections, and embedding the B mode images in the same three dimensional coordinate system (furthermore, by voxelizing the B mode images embedded in the same three dimensional coordinate system). Furthermore, the three dimensional data set may be a three dimensional data set obtained by applying registration to the plurality of B mode images for each of the plurality of B cross sections in such a three dimensional data set, or may be a three dimensional data set obtained by further applying emphasizing processing to it. Alternatively, in the case where the speed of OCT scan is sufficiently fast, or in the case where fixation and/or tracking of the subject's eye can be performed with sufficient accuracy, a plurality of three dimensional data sets arranged in a time series manner acquired through iterative scan of substantially the same three dimensional region of the subject's eye can be used.

In addition, the display controller (11) displays a cross section position indicator (CPM) that indicates the position of the cross section corresponding to the B mode image (BO) over at least one of the one or more front images (FA1 to FA3, or FO1 to FO3).

When an operation for moving the cross section position indicator (CPM) using the operation unit (50) is performed, the display controller (11), in accordance with the operation, synchronously performs the change in the display position of the cross section position indicator (CPM) and the update of the display of each of the B mode image (BO) and the blood vessel enhanced image (BA).

According to such an embodiment, the user can refer to the B mode image (BO) and the blood vessel enhanced image (BA) representing the same cross section and the one or more front images (FA1 to FA3, or FO1 to FO3). Therefore, a comprehensive ophthalmic diagnostic imaging can be achieved. In addition, the user can easily recognize the positional relationship between the B mode image (BO) and the front images (FA1 to FA3, or FO1 to FO3) via the cross section position indicator (CPM). Furthermore, since the cross section represented by the B mode image (BO) and the blood vessel enhanced image (BA) can be automatically changed according to the movement operation of the cross section position indicator (CPM), observation of a desired cross section can be performed in an easy and prompt manner. For example, in the case of performing observation while switching display images as necessary, it is possible to re-display the image displayed previously and the image displayed before the previous image, to display in parallel a plurality of images to which similar parameter setting has been applied, or the like. As a result, the observation can be performed smoothly.

The ophthalmic image display device of the embodiment may further include the following elements: a storage unit (20) configured to store the three dimensional data set; and an image forming unit (the data processor 40) configured to form the B mode image (BO), the blood vessel enhanced image (BA), and the front images (FA1 to FA3, or FO1 to FO3) based on the three dimensional data set.

The present invention also includes an embodiment of an ophthalmic image display device that does not include such a storage unit and an image forming unit. In such an embodiment, the storage unit and the image forming unit are provided in an external computer capable of communicating with the ophthalmic image display device. The ophthalmic image display device communicates with the external computer in real time, thereby performing various kinds of processing according to the embodiment.

In the embodiment, the display controller (11) is capable of displaying, as the front images, a morphological front image (FO1 to FO3) based on a slice of the three dimensional data set that intersects the cross section of the B mode image (BO) and a blood vessel enhanced front image (FA1 to FA3) based on a slice of the three dimensional data set that intersects the cross section of the B mode image (BO). As a result, it is possible to observe both the morphology of the subject's eye and the state of the blood vessel as front images.

In the above embodiment, morphological front images (FO1 to FO3) are displayed in the OCT mode, and blood vessel enhanced front images (FA1 to FA3) are displayed in the angiogram mode. In other words, the above embodiment is configured in such a manner that the display of the morphological front images (FO1 to FO3) and the display of the blood vessel enhanced front images (FA1 to FA3) are switched in accordance with the selection of the image display mode. As another embodiment, it is possible to provide a GUI capable of displaying one or more morphological front images and one or more blood vessel enhanced front images in parallel.

In the embodiment, the display controller (11) displays two or more front images (FA1 to FA3, or FO1 to FO3) respectively representing two or more different sites of the subject's eye, in parallel. As a result, various sites of the subject's eye can be simultaneously observed as front images. In the above embodiment, it is possible to set a site (e.g., a tissue, or an area) to be represented by each of the front images in an arbitrary manner.

In the embodiment, the display controller (11) displays a software key for changing the area of the slice represented by a front image (FA1 to FA3, or FO1 to FO3) at a position adjacent to the front image (FA1 to FA3, or FO1 to FO3). In addition, the display controller (11) updates the display of the corresponding front image in accordance with an operation performed using the software key. As a result, the user can easily and promptly display a desired front image.

In the above embodiment, the following elements correspond to such a software key:

the software key group provided between the front image display region 1020 and the B mode angiogram display region 1050, and used for performing operations relating to the image (FA1 or FO1) displayed in the front image display region 1020;

the software key group provided between the front image display region 1030 and the B mode image display region 1060, and used for performing operations relating to the image (FA2 or FO2) displayed in the front image display region 1030; and the software key group provided between the front image display region 1040 and the operation region 1010, and used for performing operations relating to the image (FA3 or FO3) displayed in the front image display region 1040.

Each of the software key groups includes two pull-down menus for setting the upper edge and the lower edge of a slice and software keys for setting offsets from the positions set using the respective pull-down menus.

Another aspect of the ophthalmic image display device of the embodiment will be described. The ophthalmic image display device (1) of the embodiment includes at least a display controller (11) configured to display information on a display means (the display device 2) and an operation unit (50), and is configured to be capable of performing the following processing.

The display controller (11) displays a first front image (HA1 to HA3, or HO1 to HO3) formed based on a three dimensional data set acquired through iterative application of OCT to a subject's eye in a first display region (2050 to 2070) together with a first software key (e.g., a software key group) for changing the area of the slice corresponding to the first front image. Further, the display controller (11) displays a second front image (GA1 or GO1) and a B mode image (CA or CO) individually formed based on the three dimensional data set in a second display region (2020 and 2040). Furthermore, the display controller (11) displays a cross section position indicator (CPM) that indicates the position of the cross section of the B mode image (CA or CO) over the second front image (GA1 or G01). In addition, the display controller (11) displays a third front image (GA2 or GO2) formed based on the three dimensional data set in a third display region (2030) together with a second software key (e.g., a software key group) for changing the area of the slice corresponding to the third front image.

When an operation has been performed using the first software key in the first display region (2050 to 2070), the display controller (11) updates, in accordance with this operation, the display of the first front image (HA1 to HA3, or HO1 to HO3).

In addition, when an operation for determining the area of the slice of the first front image (for example, HA1) has been performed using the operation unit (50) (e.g., when the operation on the "Apply" button has been performed), the display controller (11) displays the concerned first front image (for example, HA1) in the second display region (2020) as the second front image (for example, GA1), and displays a slice indicator (SM) indicating the area of the slice corresponding to the concerned first front image (for example, HA1) over the B mode image (for example, CA).

When an operation has been performed for moving the cross section position indicator (CPM) using the operation unit (50), the display controller (11), in accordance with the operation, synchronously performs the change in the display position of the cross section position indicator (CPM) and the update of the display of the B mode image (CA or CO).

When an operation has been performed using the second software key in the third display region (2030), the display controller (11), in accordance with this operation, performs the update of the display of the third front image (GA2 or GO2).

According to such an embodiment, the user can set a slice to obtain a desired first front image (HA1 to HA3, or HO1 to H03), and (selectively) display the first front image (HA1 to HA3, or HO1 to H03) as the second front image (GA1 or GO1) for observation. In addition, the user can arbitrarily set a cross section in the second front image (GA1 or GO1) and observe the B mode image (CA or CO) representing the set cross section. Also, the slice indicator (SM) indicating the area of the slice of the second front image (GA1 or GO1) is presented on the B mode image (CA or CO). Therefore, the subject's eye can be observed in detail with the second front image (GA1 or GO1) and the B mode image (CA or CO). Furthermore, it is also possible to simultaneously observe the third front image (GA2 or GO2) for which a slice can be arbitrarily set separately from the second front image (GA1 or GO1). According to such an embodiment, it is possible to facilitate and speed up ophthalmic diagnostic imaging.

In the embodiment, when an operation for moving the slice indicator (SM) presented on a B mode image (CA or CO) is performed using the operation unit (50), the display controller (11), in accordance with this operation, can synchronously perform the change in the display position of the slice indicator (SM) and the update of the display of the second front image (GA1 or GO1). With this, it becomes possible to easily display the second front image (GA1 or GO1) of a slice as desired. In addition, it is possible to easily perform adjustment of a slice for obtaining the second front image (GA1 or GO1) as desired. It should be noted that the movement of a slice includes a movement in a state where the slice thickness is fixed and a movement accompanying a change in the slice thickness. Furthermore, the movement of a slice includes a parallel movement of the slice and a rotational movement of the slice.

In the embodiment, the display controller (11) displays two or more first front images (HA1 to HA3, or HO1 to HO3) respectively representing two of more different sites of the subject's eye individually formed based on the three dimensional data set in the first display region (2050 to 2070) together with the first software key corresponding to each of the two or more first front images (HA1 to HA3, or HO1 to HO3). With this, for example, the user can set two or more first front images (HA1 to HA3, or HO1 to HO3) that have different slices from one another, and selectively display and observe them as the second front image (GA1, or GO1).

The ophthalmic image display device of the embodiment may further include the following elements: a storage unit (20) configured to store the three dimensional data set; an image forming unit (data processor 40) configured to form the first front image (HA1 to HA3, or HO1 to HO3), the second front image (GA1 or GO1), the B mode image (CA or CO), and the third front image (GA2 or GO2) based on the three dimensional data set.

The present invention also includes an embodiment of an ophthalmic image display device that does not include such a storage unit and an image forming unit. In such an embodiment, the storage unit and the image forming unit are provided in an external computer capable of communicating with the ophthalmic image display device. The ophthalmic image display device communicates with the external computer in real time, thereby performing various kinds of processing according to the embodiment.

In the embodiment, the display controller (11) is capable of displaying a morphological front image based on a slice of the three dimensional data set that intersects the cross section of the B mode image (CA or CO) and a blood vessel enhanced front image based on a slice of the three dimensional data set that intersects the cross section of the B mode image as the second front image (GA1 or GO1) and the third front image (GA2 or GO2). As a result, it becomes possible to observe both the morphology of the subject's eye and the state of the blood vessel as front images.

In the above embodiment, morphological front images (GO1 and GO2) are displayed in the OCT mode, and blood vessel enhanced front images (GA1 and GA2) are displayed in the angiogram mode. In other words, in the above embodiment, the display of the morphological front images (GO1 and GO2) and the display of the blood vessel enhanced front images (GA1 and GA2) are switched in accordance with the selection of the image display mode. As another embodiment, it is possible to provide a GUI capable of displaying one or more morphological front images and one or more blood vessel enhanced front images in parallel.

The actions and the effects of the embodiments are not limited to the above, and the actions and the effects provided by each of the items described in the embodiments, and the actions and the effects provided by any combination of a plurality of items should also be taken into consideration.

<Ophthalmic Imaging Device>

Figure 9:
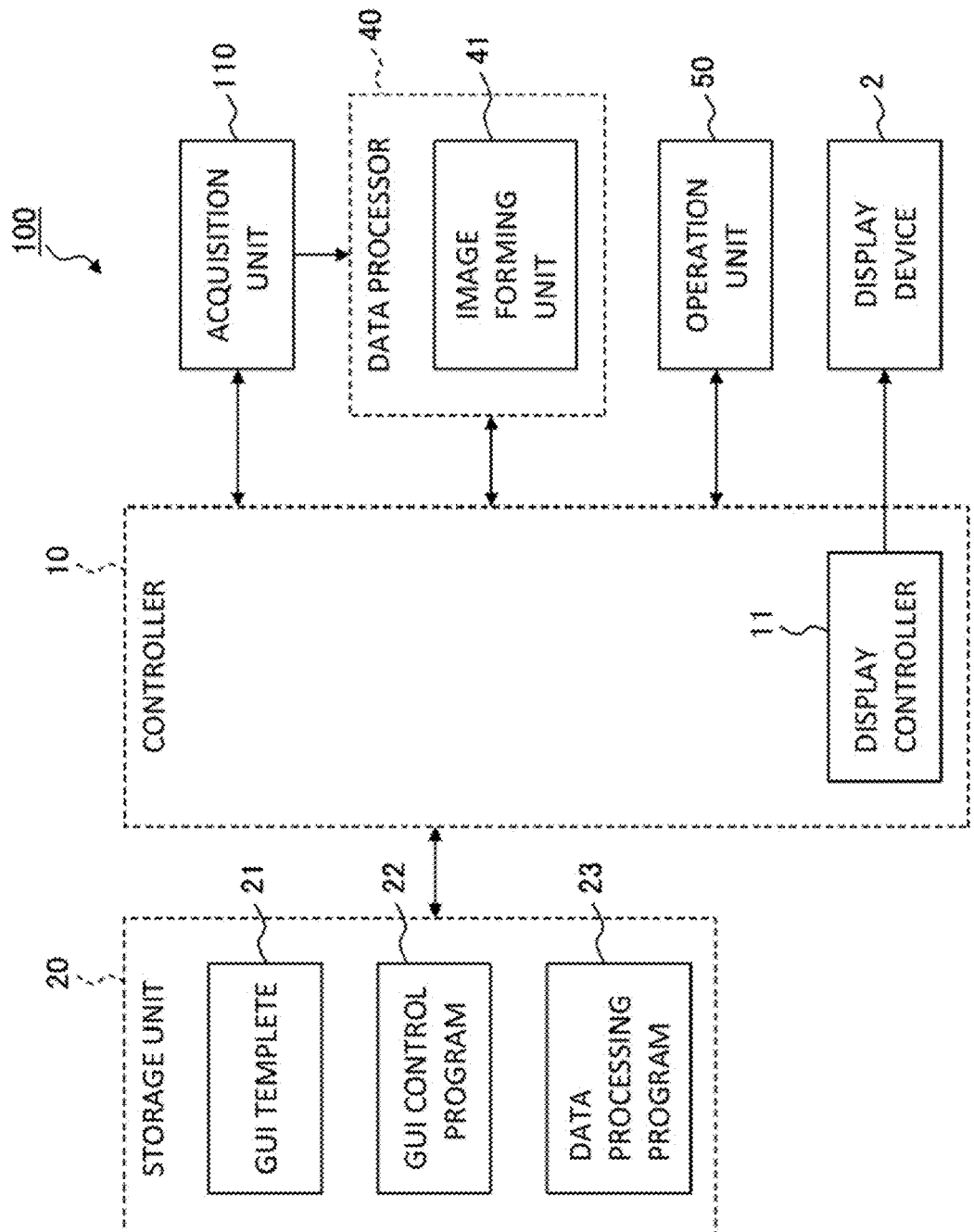
FIG. 9 is a schematic diagram illustrating an example of the configuration of an ophthalmic imaging device according to an embodiment.

The ophthalmic imaging device according to the embodiment may include part or all of the ophthalmic image display device of the above embodiment, for example. An exemplary configuration of the ophthalmic imaging device is shown in FIG. 9. Components similar to those of the ophthalmic image display device 1 in the above embodiment (illustrated in FIG. 1) are denoted by the same reference symbols, and explanations thereof are omitted unless otherwise mentioned.

The ophthalmic imaging device 100 has a function of acquiring data of the subject's eye using OCT, and a function of displaying a GUI for observing images of the subject's eye and various kinds of information relating to the subject's eye on the display device 2. The display device 2 may be a part of the ophthalmic imaging device 100 or may be an external device connected to the ophthalmic imaging device 100.

The ophthalmic imaging device 100 includes the controller 10, the storage unit 20, the data processor 40, the operation unit 50, and the acquisition unit 110. The controller 10, the storage unit 20, the data processor 40, and the operation unit 50 may include at least the same functions as those in the ophthalmic image display device 1 of the above embodiment.

The acquisition unit 110 is configured to acquire a three dimensional data set by applying OCT to a subject's eye. The acquisition unit 110 includes, for example, a configuration (e.g., an optical system, a drive system, a control system, and the like) for performing measurement using the spectral domain OCT or the swept source OCT, and a configuration for forming image data based on the data acquired using OCT. The image data forming processing includes processing such as noise removal (or noise reduction), filter processing, Fast Fourier Transform (FFT), and the like in the same manner as in the conventional OCT technique, for example.

The acquisition unit 110 is configured to scan a three dimensional region of the subject's eye. The scan mode at that time is, for example, a raster scan (or, three dimensional scan). This raster scan is executed, for example, such that each of a plurality of B cross sections is scanned a predetermined number of times, that is, such that a plurality of B cross sections is sequentially scanned a predetermined number of times. The acquisition unit 110 forms a plurality of cross section images (i.e., B scan images) for each of the B cross sections based on the data acquired through the raster scan. By embedding these cross section images in a single three dimensional coordinate system, stack data is formed. In this stack data, a predetermined number of cross section images are assigned to each of the B cross sections. In addition, volume data (or, voxel data) is formed by performing interpolation processing or the like on this stack data. For this volume data as well, a predetermined number of voxel groups are assigned to the location corresponding to each of the B cross sections. The stack data and the volume data are examples of the three dimensional data set.

Based on the three dimensional data set acquired in such a manner, the ophthalmic imaging device 100 provides the same GUI and the same control as those provided by the ophthalmic image display device 1 of the above embodiment. In order to do that, the image forming unit 41 provided in the data processor 40 operates. The image forming unit 41 forms a front image and a B mode image based on the three dimensional data set. Conditions for forming these images (e.g., a condition relating to a slice, a condition relating to a cross section position, a condition relating to image quality, or the like) may be the same as the conditions of image forming processing in the ophthalmic image display device 1 of the above embodiment.

In this way, it can be said that the ophthalmic imaging device 100 is configured in such a manner that an acquisition unit (the OCT function) and an image forming unit (the rendering function) are added to the ophthalmic image display device according to the above embodiment, or that the ophthalmic imaging device 100 is configured in such a manner that an acquisition unit (the OCT function) is added to the ophthalmic image display device according to the above embodiment.

According to such an ophthalmic imaging device 100, as in the case of the ophthalmic image display device 1 of the above embodiment, it is possible to facilitate and speed up ophthalmic diagnostic imaging.

The configurations described above are only examples for suitably carrying out the present invention. Therefore, any changes (e.g., omissions, substitutions, additions, or the like) within the scope of the gist of the present invention can be applied as appropriate.

What is claimed is:

1. An ophthalmic image display device comprising a display controller configured to display information on a display means, and an operation unit,
   wherein the display controller
      displays a B mode image, a blood vessel enhanced image representing a same cross section as the B mode image, the blood vessel enhanced image formed based on a plurality of optical coherence tomography data acquired through iteratively scanning substantially a same area of a subject's eye, and one or more front images individually formed based on a three dimensional data set acquired by performing optical coherence tomography on the subject's eye in a predetermined layout,
      displays a cross section position indicator that indicates a position of a cross section of the B mode image over at least one of the one or more front images, and
      synchronously performs changing of a display position of the cross section position indicator and updating of a display of each of the B mode image and the blood vessel enhanced image in accordance with an operation for moving the cross section position indicator performed using the operation unit.

2. The ophthalmic image display device of claim 1, further comprising:
   a storage unit configured to store the three dimensional data set; and
   an image forming unit configured to form the B mode image, the blood vessel enhanced image and the front images based on the three dimensional data set.

3. The ophthalmic image display device of claim 1, wherein the display controller is capable of displaying, as the front images, a morphological front image based on a slice of the three dimensional data set that intersects the cross section of the B mode image and a blood vessel enhanced front image based on a slice of the three dimensional data set that intersects the cross section of the B mode image.

4. The ophthalmic image display device of claim 1, wherein the display controller displays two or more front images respectively representing two or more different sites of the subject's eye in parallel.

5. The ophthalmic image display device of claim 1, wherein the display controller displays a software key for changing an area of a slice represented by a front image at a position adjacent to this front image and updates a display of this front image to form a new front image in accordance with an operation performed using the software key, wherein the slice corresponds to a subset of the three dimensional data set.

6. The ophthalmic image display device of claim 2, wherein the display controller is capable of displaying, as the front images, a morphological front image based on a slice of the three dimensional data set that intersects the cross section of the B mode image and a blood vessel enhanced front image based on a slice of the three dimensional data set that intersects the cross section of the B mode image.

7. The ophthalmic image display device of claim 2, wherein the display controller displays two or more front images respectively representing two or more different sites of the subject's eye in parallel.

8. The ophthalmic image display device of claim 3, wherein the display controller displays two or more front images respectively representing two or more different sites of the subject's eye in parallel.

9. The ophthalmic image display device of claim 2, wherein the display controller displays a software key for changing an area of a slice represented by a front image at a position adjacent to this front image and updates a display of this front image in accordance with an operation performed using the software key.

10. The ophthalmic image display device of claim 3, wherein the display controller displays a software key for changing an area of a slice represented by a front image at a position adjacent to this front image and updates a display of this front image in accordance with an operation performed using the software key.

11. An ophthalmic imaging device comprising:
an acquisition unit configured to acquire a three dimensional data set by performing optical coherence tomography on a subject's eye;
an image forming unit configured to form a B mode image, one or more front images based on the three dimensional data set, and a blood vessel enhanced image based on a plurality of optical coherence tomography data acquired through iteratively scanning substantially a same area of the subject's eye, the blood vessel enhanced image representing a same cross section as the B mode image;
a display controller configured to display information on a display means; and
an operation unit;
wherein the display controller
displays the B mode image, the blood vessel enhanced image and the front image in a predetermined layout,
displays a cross section position indicator that indicates a position of a cross section of the B mode image over at least one of the one or more front images, and
synchronously performs changing of a display position of the cross section position indicator and updating of a display of each of the B mode image and the blood vessel enhanced image in accordance with an operation for moving the cross section position indicator performed using the operation unit.

12. An ophthalmic image display device comprising a display controller configured to display information on a display means, and an operation unit,
wherein the display controller
displays a first front image formed based on a three dimensional data set acquired by performing optical coherence tomography on a subject's eye in a first display region together with a first software key for changing an area of a slice of the first front image,
displays a second front image and a B mode image individually formed based on the three dimensional data set in a second display region,
displays a cross section position indicator that indicates a position of a cross section of the B mode image over the second front image,
displays a third front image formed based on the three dimensional data set in a third display region together with a second software key for changing an area of a slice of the third front image,
updates a display of the first front image in accordance with an operation performed using the first software key,
when an operation for determining an area of a slice of the first front image has been performed using the operation unit, displays this first front image in the second display region as the second front image, and displays a slice indicator indicating an area of a slice of this first front image over the B mode image,
in accordance with an operation for moving the cross section position indicator performed using the operation unit, synchronously performs changing of a display position of the cross section position indicator and updating of a display of the B mode image, and
updates a display of the third front image in accordance with an operation performed using the second software key.

13. The ophthalmic image display device of claim 12, wherein the display controller synchronously performs changing of a display position of the slice indicator and updating of a display of the second front image in accordance with an operation for moving the slice indicator performed using the operation unit.

14. The ophthalmic image display device of claim 12, wherein the display controller displays two or more first front images respectively representing two of more different sites of the subject's eye individually formed based on the three dimensional data set in the first display region together with two or more first software keys respectively corresponding to the two or more first front images.

15. The ophthalmic image display device of claim 12, further comprising:
a storage unit configured to store the three dimensional data set; and
an image forming unit configured to form the first front image, the second front image, the B mode image, and the third front image based on the three dimensional data set.

16. The ophthalmic image display device of claim 12, wherein the display controller is capable of displaying, as the second front image and the third front image, a morphological front image based on a slice of the three dimensional data set that intersects the cross section of the B mode image and a blood vessel enhanced front image based on a slice of the three dimensional data set that intersects the cross section of the B mode image.

17. An ophthalmic imaging device comprising:
an acquisition unit configured to acquire a three dimensional data set by performing optical coherence tomography on a subject's eye;
an image forming unit configured to be capable of forming a B mode image and a front image based on the three dimensional data set; and
a display controller configured to display information on a display means; and
an operation unit;
wherein the display controller
displays a first front image formed based on the three dimensional data set in a first display region together with a first software key for changing an area of a slice of the first front image, displays a second front image and a B mode image individually formed based on the three dimensional data set in a second display region, displays a cross section position indicator that indicates a position of a cross section of the B mode image over the second front image, displays a third front image formed based on the three dimensional data set in a third display region together with a second software key for changing an area of a slice of the third front image, updates a display of the first front image in accordance with an operation performed using the first software key, when an operation for determining an area of a slice of the first front image has been performed using the operation unit, displays this first front image in the second display region as the second front image, and displays a slice indicator indicating an area of a slice of this first front image over the B mode image, in accordance with an operation for moving the cross section position indicator performed using the operation unit, synchronously performs changing of a display position of the cross section position indicator and updating of a display of the B mode image, and updates a display of the third front image in accordance with an operation performed using the second software key.

18. The ophthalmic image display device of claim 13, wherein the display controller displays two or more first front images respectively representing two of more different sites of the subject's eye individually formed based on the three dimensional data set in the first display region together with two or more first software keys respectively corresponding to the two or more first front images.

19. The ophthalmic image display device of claim 13, further comprising:

a storage unit configured to store the three dimensional data set; and an image forming unit configured to form the first front image, the second front image, the B mode image, and the third front image based on the three dimensional data set.

20. The ophthalmic image display device of claim 14, further comprising:

a storage unit configured to store the three dimensional data set; and an image forming unit configured to form the first front image, the second front image, the B mode image, and the third front image based on the three dimensional data set.

* * * * *

UNITED STATES PATENT AND TRADEMARK OFFICE
CERTIFICATE OF CORRECTION

PATENT NO. : 10,426,335 B2
APPLICATION NO. : 15/565542
DATED : October 1, 2019
INVENTOR(S) : Masahiro Akiba and Atsushi Kubota Page 1 of 1

It is certified that error appears in the above-identified patent and that said Letters Patent is hereby corrected as shown below:

On the Title Page

Column 1, item (72), the residence information for inventor Masahiro Akiba "Toda (JP);" should read --Toda-shi, Saitama (JP)--;

Column 1, item (72), the residence information for inventor Atsushi Kubota "Tokyo (JP)" should read --Itabashi-ku, Tokyo (JP)--.

Signed and Sealed this
Third Day of March, 2020

Andrei Iancu
*Director of the United States Patent and Trademark Office*